US008598222B2

(12) United States Patent  
Wolf et al.

(10) Patent No.: US 8,598,222 B2
(45) Date of Patent: Dec. 3, 2013

(54) METHOD FOR PREPARING 1,3,4-SUBSTITUTED PYRAZOL COMPOUNDS

(75) Inventors: Bernd Wolf, Fußgönheim (DE); Volker Maywald, Ludwigshafen (DE); Michael Keil, Freinsheim (DE); Christopher Koradin, Ludwigshafen (DE); Michael Rack, Eppelheim (DE); Thomas Zierke, Böhl-Iggelheim (DE); Martin Sukopp, Mannheim (DE)

(73) Assignee: BASF SE, Ludwigshafen (DE)

( * ) Notice: Subject to any disclaimer, the term of this patent is extended or adjusted under 35 U.S.C. 154(b) by 331 days.

(21) Appl. No.: 12/990,340

(22) PCT Filed: May 4, 2009

(86) PCT No.: PCT/EP2009/055328
§ 371 (c)(1),
(2), (4) Date: Dec. 13, 2010

(87) PCT Pub. No.: WO2009/135808
PCT Pub. Date: Nov. 12, 2009

(65) Prior Publication Data
US 2011/0172436 A1  Jul. 14, 2011

(30) Foreign Application Priority Data

May 5, 2008 (EP) .................................. 08155657

(51) Int. Cl.
*A61K 31/415* (2006.01)
*C07D 231/14* (2006.01)

(52) U.S. Cl.
USPC ....................... 514/406; 548/374.1

(58) Field of Classification Search
USPC ....................... 548/374.1; 514/406
See application file for complete search history.

(56) References Cited

U.S. PATENT DOCUMENTS

| 5,093,347 A | 3/1992 | Graneto et al. |
| 5,330,995 A | 7/1994 | Eicken et al. |

(Continued)

FOREIGN PATENT DOCUMENTS

| EP | 0 545 099 | 6/1993 |
| EP | 0 581 725 | 2/1994 |

(Continued)

OTHER PUBLICATIONS

Aldabbagh, F., "Acid Halides", in Comprehensive Organic Functional Group Transformations II, 2005, vol. 5, p. 1-17, Katritzky, Alan R., Taylor, Richard, J.K. Eds. Elsevier Ltd. Oxford, UK.

Office Action dated Nov. 14, 2012, in co-pending U.S. Appl. No. 12/990,364.

(Continued)

*Primary Examiner* — Kamal Saeed
*Assistant Examiner* — Janet L Coppins
(74) *Attorney, Agent, or Firm* — Brinks Gilson & Lione

(57) ABSTRACT

The present invention relates to a process for preparing 1,3-substituted pyrazole compounds of the formula I

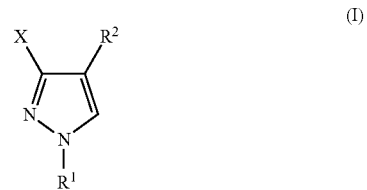

in which
X is especially a $CX^1X^2X^3$ group in which
$X^1$, $X^2$ and $X^3$ are each independently especially hydrogen, fluorine or chlorine,
$R^1$ is $C_1$-$C_4$-alkyl or cyclopropyl, and
$R^2$ is hydrogen, CN or a $CO_2R^{2a}$ group in which
$R^{2a}$ is especially $C_1$-$C_6$-alkyl,
comprising the following steps:
i) reacting a compound of the formula II with a hydrazone of the formula III

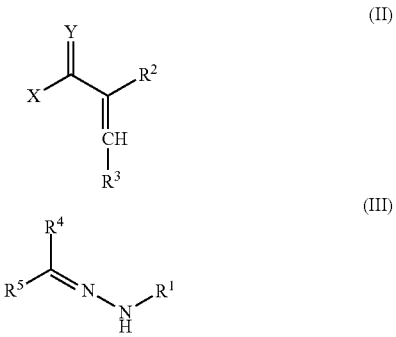

where the variables X and $R^2$ in formula II are each as defined for formula I,
Y is oxygen, an $NR^{y1}$ group or an $[NR^{y2}R^{y3}]^+Z^-$ group,
$R^3$ is $OR^{3a}$ or an $NR^{3b}R^{3c}$ group,
and where the variable $R^1$ in formula III is as defined for formula I,
$R^4$ and $R^5$ are each independently hydrogen, $C_1$-$C_6$-alkyl, optionally substituted phenyl, where at least one of the $R^4$ and $R^5$ radicals is different from hydrogen, and where $R^4$ and $R^5$ together with the carbon atom to which they are bonded may also be a 5- to 10-membered saturated carbocycle;
ii) treating the reaction product obtained with an acid in the presence of water.

23 Claims, No Drawings

(56) References Cited

U.S. PATENT DOCUMENTS

| | | |
|---|---|---|
| 5,340,837 A | 8/1994 | Hall et al. |
| 5,438,070 A | 8/1995 | Eicken et al. |
| 5,498,624 A | 3/1996 | McLoughlin et al. |
| 5,618,951 A | 4/1997 | Britton |
| 6,706,911 B1 | 3/2004 | Lui et al. |
| 7,358,387 B2 | 4/2008 | Lantzsch et al. |
| 7,388,097 B2 | 6/2008 | Elbe et al. |
| 7,501,527 B2 | 3/2009 | Lantzsch et al. |
| 7,521,397 B2 | 4/2009 | Dunkel et al. |
| 7,585,998 B2 | 9/2009 | Gallenkamp et al. |
| 7,863,460 B2 | 1/2011 | Aihara et al. |
| 7,939,673 B2 | 5/2011 | Pazenok et al. |
| 7,994,207 B2 | 8/2011 | Zierke et al. |
| 8,115,012 B2 | 2/2012 | Sukopp et al. |
| 2005/0033095 A1 | 2/2005 | Nappa et al. |
| 2005/0234244 A1 | 10/2005 | Bartolini et al. |
| 2006/0252944 A1 | 11/2006 | Lantzsch et al. |
| 2008/0108686 A1 | 5/2008 | Gewehr et al. |
| 2009/0105316 A1 | 4/2009 | Dunkel et al. |
| 2009/0123561 A1 | 5/2009 | Gewehr et al. |
| 2009/0233795 A1 | 9/2009 | Dietz et al. |
| 2009/0326242 A1 | 12/2009 | Pazenok et al. |
| 2010/0022782 A1 | 1/2010 | Zierke et al. |
| 2010/0069646 A1 | 3/2010 | Sukopp et al. |
| 2010/0174094 A1 | 7/2010 | Zierke et al. |
| 2010/0184994 A1 | 7/2010 | Nett et al. |
| 2010/0204483 A1 | 8/2010 | Pazenok et al. |
| 2010/0215777 A1 | 8/2010 | Pohlman et al. |
| 2010/0274049 A1 | 10/2010 | Lui et al. |
| 2011/0040096 A1 | 2/2011 | Zierke et al. |
| 2011/0046371 A1 | 2/2011 | Zierke et al. |
| 2011/0172436 A1 | 7/2011 | Wolf et al. |

FOREIGN PATENT DOCUMENTS

| | | | |
|---|---|---|---|
| EP | 0 589 301 | 3/1994 | |
| EP | 1854788 | 11/2007 | |
| EP | 2 042 482 | 4/2009 | |
| EP | 2 072 497 | 6/2009 | |
| JP | 266612 | 2/1989 | |
| JP | 2000/212166 | 8/2000 | |
| JP | 01113371 | 4/2001 | |
| WO | WO 92/12970 | 8/1992 | |
| WO | WO 93/11117 | 6/1993 | |
| WO | WO 03/051820 | 6/2003 | |
| WO | WO 03/066610 | 8/2003 | |
| WO | WO 03/070705 | 8/2003 | |
| WO | WO 2005/003077 | 1/2005 | |
| WO | WO 2005/042468 | 5/2005 | |
| WO | WO 2005/044804 | 5/2005 | |
| WO | WO 2005/123690 | 12/2005 | |
| WO | WO 2006/024389 | 3/2006 | |
| WO | WO 2006/090778 | 8/2006 | |
| WO | WO 2007/003603 | 1/2007 | |
| WO | WO 2007/006806 | 1/2007 | |
| WO | WO 2007/031323 | 3/2007 | |
| WO | WO 2008/022777 | 2/2008 | |
| WO | WO 2008/053043 | 5/2008 | |
| WO | WO 2008/077907 | 7/2008 | |
| WO | WO 2008/113660 | 7/2008 | |
| WO | WO 2008/145740 | 12/2008 | |
| WO | WO 2008/152138 | 12/2008 | |
| WO | WO-2008/152138 * | 12/2008 | ........... C07D 231/14 |
| WO | WO 2008/152138 A2 * | 12/2008 | ........... C07D 231/14 |
| WO | WO 2009/133178 | 11/2009 | |
| WO | WO 2009/133179 | 11/2009 | |
| WO | WO 2010/009990 | 1/2010 | |

OTHER PUBLICATIONS

Pryadeina, M.V. et al., "Synthesis and Structure of 2-ethoxy- and 2-aminomethylidene 3-fluoroalkyl-3-oxopropionates," Russian Journal of Organic Chemistry, vol. 43, No. 7, 2007, pp. 945-955 (XP002557997).

Nagarajan, K., et al., "Synthesis abd Structures of Pyrazoles from Ethoxymethylene Derivatives of 1,3-dicarbonyl Compounds and Hydrazines", J. Chem. Research, 1986, p. 166-167, vol. 5.

International Search Report in International Application No. PCT/EP2009/055328.

English language translation of the International Preliminary Report on Patentability from corresponding International Application No. PCT/EP2009/055328.

Altenbach, Robert J. et al., "Synthesis, Potency, and In Vivo Profiles of Quinoline Containing Histamine $H_3$ Receptor Inverse Agonists", J. Med. Chem., 2007, pp. 5439-5448, vol. 50.

Etsuji, Okada, et al., "Facile Synthetic Methods for 3- ad 5-trifluoromethyl-4-trifluoroacetyl-pyrazoles and Their Conversion into Pyrazole-4-carobxylic Acids", Heterocycles, , 1992, p. 791-798, vol. 34, No. 4.

Vinogradova, Khimiya, et al. "Synthesis and Mechanism of the Formation of Bis(Methylamides) of Pyrazoledicarboxylic Acids", Chemistry of Heterocyclic Compounds, Jan. 1, 1968, p. 502-507, vol. 4.

* cited by examiner

METHOD FOR PREPARING 1,3,4-SUBSTITUTED PYRAZOL COMPOUNDS

This application is a National Stage application of International Application No. PCT/EP2009/055328, filed May 4, 2009, the entire contents of which is hereby incorporated herein by reference. This application also claims priority under 35 U.S.C. §119 to European Patent Application No. 08155657.3, filed May 5, 2008, the entire contents of which is hereby incorporated herein by reference.

The present invention relates to a process for preparing 1,3,4-substituted pyrazole compounds of the formula I

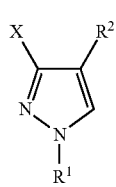

in which
X is a $CX^1X^2X^3$ group in which
$X^1$, $X^2$ and $X^3$ are each independently hydrogen, fluorine or chlorine, where $X^1$ may also be $C_1$-$C_6$-alkyl or $C_1$-$C_4$-haloalkyl and where at least one of the $X^1$, $X^2$ radicals is different from hydrogen,
$R^1$ is $C_1$-$C_4$-alkyl or cyclopropyl, and
$R^2$ is CN or a $CO_2R^{2a}$ group in which
$R^{2a}$ is $C_5$-$C_6$-cycloalkyl, optionally substituted phenyl or $C_1$-$C_6$-alkyl which may optionally be substituted by $C_1$-$C_4$-alkoxy, phenyl or $C_3$-$C_6$-cycloalkyl.

Pyrazoles of the general formula I are important starting materials for a number of active pharmaceutical ingredients and crop protection active ingredients, especially for 1,3-substituted pyrazol-4-ylcarboxanilides, as described, for example, in U.S. Pat. No. 5,498,624, EP 545099 A1, EP 589301 A1, WO 92/12970, WO 03/066610, WO 2006/024389, WO 2007/003603, WO 2007/006806.

1,3,4-substituted pyrazole compounds of the formula I are prepared typically by cyclizing suitable 1,3-difunctional compounds with substituted hydrazine compounds, or by reacting 1,3-difunctional compounds with hydrazine, followed by an alkylation to introduce the substituent on the nitrogen (1 position). A fundamental disadvantage in this procedure is the lack of regioselectivity of the cyclization of 1,3-difunctional compounds with substituted hydrazine compounds, and also the lack of regioselectivity of the N-alkylation of pyrazoles, such that, in both cases, not only the desired 1,3,4-substituted pyrazole compound of the formula I (1,3 isomer) but also the 1,4,5-substituted isomer of the formula I' (1,5 isomer) is formed.

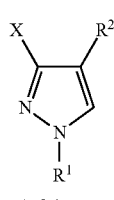

1, 3-isomer

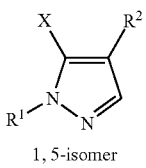

1, 5-isomer

Regardless of the fact that the lack of selectivity leads to yield losses, 1,3-isomer of the formula I and 1,5-isomer of the formula I' can frequently be separated only with difficulty. In order to achieve acceptable selectivities, the reactions therefore have to be carried out at low temperatures, which considerably increases the apparatus complexity. In addition, the regioselectivity is also not entirely satisfactory under cold conditions.

U.S. Pat. No. 5,498,624 and others describe a process for preparing (3-difluoromethyl-1-methyl-pyrazol-4-yl)carboxylic esters, in which α-ethoxymethylene-4,4-difluoro-3-oxobutyric ester is cyclized with methylhydrazine to give the pyrazole compound. WO 92/12970 discloses a comparable process in which 4,4-difluoro-3-oxobutyric ester is reacted gradually with triethyl orthoformate and with methylhydrazine, which forms ethoxymethylene-4,4-difluoro-3-oxobutyric ester as an intermediate. The selectivity for the desired isomer is not satisfactory.

WO 2003/051820 and WO 2005/042468 describe the cyclization of 2-haloacyl-3-aminoacrylic esters with alkylhydrazines to give 1-alkyl-3-haloalkylpyrazole-4-carboxylic esters. The selectivity for the desired isomer is not satisfactory.

WO 2008/022777 describes a process for preparing 1-substituted 3-(dihalomethyl)pyrazole-4-carboxylic esters, in which vinylogous amidinium salts, which are obtainable by reacting α-(halomethyl)difluoromethylamines with acrylates in the presence of a Lewis acid, are reacted with substituted hydrazines. The selectivity for the desired isomer is not satisfactory.

It is therefore an object of the invention to provide a process for preparing 1,3,4-substituted pyrazole compounds of the formula I cited at the outset, which affords the desired 1,3-isomer of the formula I with high yields and good selectivity.

It has been found that, surprisingly, 1,3,4-substituted pyrazole compounds of the formula I defined at the outset can be prepared in a simple manner with high yields and high regioselectivity for the desired 1,3-isomer when suitable 1,3-difunctional compounds of the formula II described below are first reacted with a hydrazone of the formula III described below and the intermediate formed is treated with an acid in the presence of water.

Accordingly, the present invention relates to a process for preparing 1,3-substituted pyrazole compounds of the formula I defined at the outset, which comprises the following steps:
i) reacting a compound of the formula II with a hydrazone of the formula III

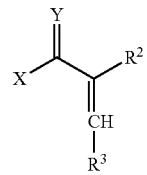

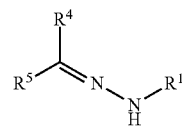

where the variables X and $R^2$ in formula II are each as defined for formula I, Y is oxygen, an $NR^{y1}$ group or an $[NR^{y2}R^{y3}]^+Z^-$ group, in which
- $R^{y1}$, $R^{y2}$ and $R^{y3}$ are each independently $C_1$-$C_6$-alkyl, $C_5$-$C_6$-cycloalkyl, optionally substituted phenyl or optionally substituted phenyl-$C_1$-$C_4$-alkyl, or
- $R^{y2}$ and $R^{y3}$ together with the nitrogen atom to which they are bonded are an N-bonded, 5- to 8-membered, saturated, optionally substituted heterocycle which, as well as the nitrogen atom, may also comprise 1 or 2 further heteroatoms selected from N, O and S as ring atoms, and
- $Z^-$ is an anion;

$R^3$ is $OR^{3a}$ or an $NR^{3b}R^{3c}$ group, in which
- $R^{3a}$, $R^{3b}$ and $R^{3c}$ are each independently $C_1$-$C_6$-alkyl, $C_5$-$C_6$-cycloalkyl, optionally substituted phenyl or optionally substituted phenyl-$C_1$-$C_4$-alkyl, or
- $R^{3b}$ and $R^{3c}$ together with the nitrogen atom to which they are bonded are an N-bonded 5- to 8-membered, saturated, optionally substituted heterocycle which, as well as the nitrogen atom, may also comprise 1 or 2 further heteroatoms selected from N, O and S as ring atoms, and where the variable $R^1$ in formula III is as defined for formula I, $R^4$ and $R^5$ are each independently hydrogen, $C_1$-$C_6$-alkyl which may optionally be substituted by $C_1$-$C_4$-alkoxy, phenyl or $C_3$-$C_6$-cycloalkyl, $C_3$-$C_6$ cycloalkyl or optionally substituted phenyl, where at least one of the $R^4$ and $R^5$ radicals is different from hydrogen, and where $R^4$ and $R^5$ together with the carbon atom to which they are bonded may also be a 5- to 10-membered saturated carbocycle which is optionally mono- or polysubstituted by $C_1$-$C_4$-alkyl groups and/or optionally substituted phenyl, and/or comprises one or 2 fused phenyl rings;

ii) treating the reaction product obtained with an acid in the presence of water.

The process according to the invention is associated with a series of advantages. Firstly, it affords the desired 1,3,4-substituted pyrazoles with a high yield and high regioselectivity based on the desired 1,3-isomer of the formula I. In addition, to achieve the desired selectivity, low temperatures are not required, and step i) and step ii) can be carried out at moderate temperatures, for example in the range from 10 to 180° C., especially in the range from 20 to 150° C. It will be appreciated that the reaction in steps i) and ii) can also be carried out at lower temperatures, for example at temperatures down to −20° C., which is, however, not required to achieve the desired regioselectivity.

In step i) of the process according to the invention, the compound of the formula VI shown below is formed, which can typically be isolated:

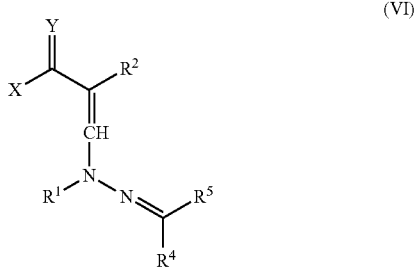

(VI)

In formula VI, X, Y, $R^1$, $R^2$, $R^4$ and $R^5$ have the definitions specified here and hereinafter. The compounds of the formula VI are novel, excluding compounds of the formula VI in which $R^4$ and $R^5$ are each optionally substituted phenyl and Y is oxygen. The latter are known from EP 581725. The novel compounds of the formula VI likewise form part of the subject matter of the present invention.

The terms used for organic groups in the definition of the variables are, for example the expression "halogen", collective terms which represent the individual members of these groups of organic units. The prefix $C_x$-$C_y$ denotes the number of possible carbon atoms in the particular case.

The term "halogen" denotes in each case fluorine, bromine, chlorine or iodine, especially fluorine, chlorine or bromine.

Examples of other definitions are:

The term "$C_1$-$C_6$-alkyl", as used herein, denotes a saturated, straight-chain or branched hydrocarbon group comprising from 1 to 6 carbon atoms, especially from 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and isomers thereof. $C_1$-$C_4$-alkyl comprises, for example, methyl, ethyl, propyl, 1-methylethyl, butyl, 1-methylpropyl, 2-methylpropyl or 1,1-dimethylethyl.

The term "$C_1$-$C_6$-alkyl", which may optionally be substituted by $C_1$-$C_4$-alkoxy, phenyl or $C_3$-$C_6$-cycloalkyl, represents unsubstituted $C_1$-$C_6$-alkyl, as defined above, or $C_1$-$C_6$-alkyl in which one of the hydrogen atoms is replaced by a $C_1$-$C_4$-alkoxy, phenyl or $C_3$-$C_6$-cycloalkyl group.

The term "$C_1$-$C_4$-haloalkyl", as used herein, describes straight-chain or branched alkyl groups having from 1 to 4 carbon atoms, in which the hydrogen atoms of these groups are replaced partly or fully by halogen atoms, especially by fluorine and/or chlorine, for example chloromethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, etc.

The term "$C_1$-$C_6$-alkoxy", as used herein, describes straight-chain or branched saturated alkyl groups comprising from 1 to 6 carbon atoms which are bonded via an oxygen atom. Examples comprise $C_1$-$C_6$-alkoxy, for example methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, etc.

The term "$C_1$-$C_4$-alkoxy-$C_1$-$C_6$-alkyl", as used herein, describes $C_1$-$C_6$-alkyl in which one of the hydrogen atoms is replaced by a $C_1$-$C_4$-alkoxy group. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)

ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)-butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethyl-ethoxy)butyl, etc.

The term "$C_3$-$C_6$-cycloalkyl", as used herein, describes monocyclic saturated hydrocarbon radicals comprising from 3 to 6 carbon atoms. Examples of monocyclic radicals comprise cyclopropyl, cyclobutyl, cyclopentyl and cyclohexyl.

The term "optionally substituted phenyl", as used herein, represents unsubstituted phenyl or describes phenyl which bears 1, 2, 3, 4 or 5 and especially 1, 2 or 3 substituents which are inert under the conditions of the reaction. Examples of inert substituents are halogen, especially fluorine, chlorine or bromine, CN, $NO_2$, $C_1$-$C_6$-alkyl, $C_1$-$C_6$-alkylthio, $C_1$-$C_6$-alkylsulfonyl, $C_1$-$C_4$-haloalkyl, $C_1$-$C_6$-alkoxy, $C_3$-$C_6$-cycloalkyl, and $C_1$-$C_4$-alkoxy-$C_1$-$C_6$-alkyl.

The term "optionally substituted phenyl-$C_1$-$C_6$-alkyl", as used herein, describes $C_1$-$C_6$-alkyl in which one of the hydrogen atoms is replaced by an optionally substituted phenyl group. Examples are benzyl, 4-methylbenzyl, phenylethyl etc.

The term "N-bonded 5- to 8-membered, saturated, optionally substituted heterocycle" represents a saturated heterocycle which is bonded via a ring nitrogen atom and has 5, 6, 7 or 8 ring atoms, where, as well as the nitrogen atom, the ring atoms may also comprise further heteroatoms, and which is unsubstituted or bears 1, 2, 3, 4 or 5 and especially 1, 2 or 3 substituents which are inert under the conditions of the reaction. Examples of inert substituents are CN, $C_1$-$C_6$-alkyl, $C_1$-$C_6$-alkylthio, $C_1$-$C_6$-alkylsulfonyl, $C_1$-$C_4$-haloalkyl, $C_1$-$C_6$-alkoxy, $C_3$-$C_6$-cycloalkyl, and $C_1$-$C_4$-alkoxy-$C_1$-$C_6$-alkyl. The heterocycle may, as well as the nitrogen atom in position 1 and the ring carbon atoms, also comprise 1 or 2 further heteroatoms selected from N, O and S as ring atoms. Examples of N-bonded, 5- to 8-membered, saturated, optionally substituted heterocycles are pyrrolidin-1-yl, piperidin-1-yl, morpholin-4-yl, piperazin-1-yl and N-methylpiperazin-1-yl.

A preferred embodiment of the invention relates to the preparation of pyrazole compounds of the formula I in which $R^2$ is $COOR^{2a}$ group in which $R^{2a}$ is as defined above and is in particular $C_1$-$C_6$-alkyl or $C_1$-$C_4$-alkoxy-$C_1$-$C_6$-alkyl and especially $C_1$-$C_4$-alkyl. Accordingly, in this embodiment, the $R^2$ group in the formulae II and VI is also a $COOR^{2a}$ group in which $R^{2a}$ is as defined above and is in particular $C_1$-$C_6$-alkyl or $C_1$-$C_4$-alkoxy-$C_1$-$C_6$-alkyl and especially $C_1$-$C_4$-alkyl.

Another embodiment of the invention relates to the preparation of pyrazole compounds of the formula I in which $R^2$ is CN. Accordingly, $R^2$ in the compounds of the formulae II and VI is also CN.

The process according to the invention is suitable especially for preparing compounds of the general formula I in which X is a $CX^1X^2X^3$ group in which $X^1$, $X^2$ and $X^3$ are each as defined above, where at least one of the $X^1$ and $X^2$ radicals is different from hydrogen. More particularly, $X^1$ and $X^2$ are each fluorine. $X^3$ is preferably hydrogen, fluorine or chlorine. Examples of preferred $CX^1X^2X^3$ radicals are dichloromethyl, chlorofluoromethyl, difluoromethyl, chlorodifluoromethyl and trifluoromethyl. In a specific embodiment, X is a $CHF_2$ group.

In addition, it has been found to be advantageous when $R^1$ in the formula I and accordingly in formula III is $C_1$-$C_4$-alkyl and especially methyl.

In a first embodiment of the invention, the pyrazole compounds of the formula I are prepared by using a compound of the formula II in which Y is oxygen. Such compounds are also referred to hereinafter as compounds IIa. Compounds of the formula IIa in which $R^2$ is a $COOR^{2a}$ group in which $R^{2a}$ is as defined above and is especially $C_1$-$C_6$-alkyl or $C_1$-$C_4$-alkoxy-$C_1$-$C_6$-alkyl and especially $C_1$-$C_4$-alkyl are also referred to hereinafter as compounds IIa.1.

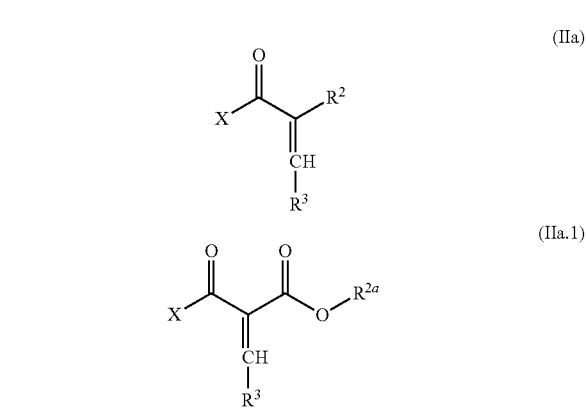

In the formulae IIa and IIa.1, $R^2$, $R^{2a}$, $R^3$ and X are each as defined above.

More particularly, X in the formulae IIa and IIa.1 is a $CX^1X^2X^3$ group in which $X^1$, $X^2$ and $X^3$ are each as defined above. In particular, at least one of the $X^1$ and $X^2$ radicals is different than hydrogen. More particularly, $X^1$ and $X^2$ are each fluorine. $X^3$ is preferably hydrogen, fluorine or chlorine. Examples of particularly preferred $CX^1X^2X^3$ groups are dichloromethyl, trifluoromethyl, chlorodifluoromethyl, fluorochloromethyl and difluoromethyl. In a specific embodiment, X is a $CHF_2$ group.

In a second embodiment of the invention, the pyrazole compounds of the formula I are prepared by using a compound of the formula II in which Y is an $[NR^{y2}R^{y3}]^+Z$ group. Such compounds are also referred to hereinafter as compounds IIb. Compounds of the formula IIb in which $R^2$ is a $COOR^{2a}$ group in which $R^{2a}$ is as defined above and is in particular $C_1$-$C_6$-alkyl or $C_1$-$C_4$-alkoxy-$C_1$-$C_6$-alkyl are also referred to hereinafter as compounds IIb.1.

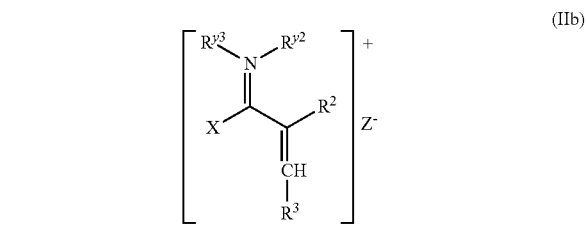

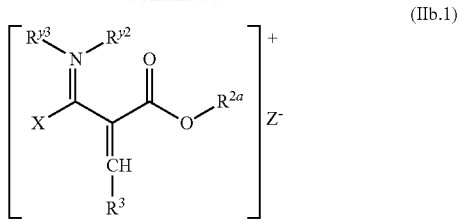

(IIb.1)

In the formulae IIb and IIb.1, $R^2$, $R^{2a}$, $R^{y2}$, $R^{y3}$, Z, $R^3$ and X are each as defined above.

More particularly, X in the formulae IIb and IIb.1 is a $CX^1X^2X^3$ group in which $X^1$, $X^2$ and $X^3$ are each as defined above. More particularly, at least one of the $X^1$ and $X^2$ radicals is different than hydrogen. More particularly, $X^1$ and $X^2$ are each fluorine. $X^3$ is preferably hydrogen, fluorine or chlorine. Examples of particularly preferred $CX^1X^2X^3$ groups are trifluoromethyl, chlorodifluoromethyl, fluorochloromethyl and difluoromethyl. More particularly, the $CX^1X^2X^3$ group in the formulae IIb, IIb.1 and IIb.2 is CHClF or $CHF_2$.

$R^{y2}$ and $R^{y3}$ are in particular $C_1$-$C_4$-alkyl and especially methyl.

$Z^-$ is an anion or an anion equivalent, which is preferably derived from a Lewis acid such as $MgF_2$, $BF_3$, $BCl_3$, $AlCl_3$, $AlF_3$, $ZnCl_2$, $PF_5$, $SbF_5$, $BiCl_3$, $GaCl_3$, $SnCl_4$, or $SiCl_4$, for example is fluoride, $[MgF_3]^-$, $[BF_4]^-$, $[BCl_3F]^-$, $[AlF_4]^-$, $[AlCl_3F]^-$, $[ZnCl_2F]^-$, $[PF6]^-$, $[SbF_6]^-$, $[BiCl_3F]^-$, $[GaCl_3F]^-$, $[SnCl_4F]^-$ or $[SiCl_4F]^-$.

In a first variant of the process according to the invention, $R^3$ in the formulae II, IIa and IIa.1, IIb and IIb.1 is an $OR^{3a}$ group. In this case, $R^{3a}$ is as defined above and is in particular $C_1$-$C_4$-alkyl and especially methyl or ethyl.

In a second variant of the process according to the invention, $R^3$ in the formulae II, IIa and IIa.1, IIb and IIb.1 is an $NR^{3b}R^{3c}$ group. In this group, $R^{3b}$ and $R^{3c}$ are each as defined above and are in particular $C_1$-$C_4$-alkyl and especially methyl or ethyl, or $R^{3b}$ and $R^{3c}$ together with the nitrogen atom to which they are bonded are an N-bonded 5- to 8-membered, saturated heterocycle which, as well as the nitrogen atom, may also have 1 or 2 further heteroatoms selected from N, O and S as ring atoms and which may optionally bear 1 or 2 $C_1$-$C_4$-alkyl groups. Examples of the latter cyclic $NR^{3b}R^{3c}$ group are pyrrolidin-1-yl, morpholin-4-yl, piperidin-1-yl and 4-methylpiperazin-1-yl.

The type of hydrazone of the formula III used in the reaction is in principle of minor significance. In principle, preference is given to those hydrazones of the formula III (and accordingly also compounds of the formula VI) in which
$R^4$ is hydrogen or $C_1$-$C_6$-alkyl and
$R^5$ is $C_1$-$C_6$-alkyl, $C_3$-$C_6$-cycloalkyl or optionally substituted phenyl, or
$R^4$ and $R^5$ together with the carbon atom to which they are bonded may be a 5- to 10-membered saturated carbocycle which is optionally mono- or polysubstituted, e.g. mono-, di-, tri- or tetrasubstituted, by $C_1$-$C_4$-alkyl groups and/or comprises a fused phenyl ring.

In a particularly preferred embodiment of the process according to the invention, a hydrazone of the formula III is used in which
$R^4$ is hydrogen or $C_1$-$C_4$-alkyl, especially hydrogen and
$R^5$ is optionally substituted phenyl.

In another particularly preferred embodiment of the process according to the invention, a hydrazone of the formula III is used in which $R^4$ and $R^5$ are each $C_1$-$C_4$-alkyl or, together with the carbon atom to which they are bonded, form a 5- to 8-membered, saturated carbocycle which is optionally substituted in the manner described above.

The expression "optionally substituted phenyl" in this context has the definitions specified above and is in particular unsubstituted phenyl, or phenyl which has 1, 2 or 3 substituents selected from halogen, especially fluorine, chlorine or bromine, nitro, cyano, $C_1$-$C_4$-alkyl, especially methyl or ethyl, and $C_1$-$C_4$-alkoxy, especially methoxy or ethoxy, for example as in 2-, 3- or 4-fluorophenyl, 2-, 3- or 4-chlorophenyl, 4-bromophenyl, 2-, 3- or 4-methylphenyl, 2-, 3-, or 4-methoxyphenyl, 4-cyanophenyl, 4-nitrophenyl.

With regard to $R^5$, the expression "optionally substituted phenyl" has the aforementioned definitions and more preferably represents unsubstituted phenyl or phenyl which has 1 or 2 substituents selected from halogen, especially chlorine, $C_1$-$C_4$-alkyl, especially methyl or ethyl, and $C_1$-$C_4$-alkoxy, especially methoxy or ethoxy, for example as in 2-, 3- or 4-chlorophenyl, 2-, 3- or 4-methylphenyl, 2-, 3- or 4-methoxyphenyl.

In a very particularly preferred configuration of the process according to the invention, a hydrazone of the formula III is used, in which
$R^4$ is hydrogen and
$R^5$ is optionally substituted phenyl, especially unsubstituted phenyl or phenyl which has 1 or 2 substituents, where the substituents are as specified above and are preferably selected from halogen, especially chlorine, $C_1$-$C_4$-alkyl, especially methyl or ethyl, and $C_1$-$C_4$-alkoxy, especially methoxy or ethoxy.

In a very particularly preferred configuration of the process according to the invention, a hydrazone of the formula III is used, in which
$R^4$ and $R^5$ together with the carbon atom to which they are bonded are a 5- to 10-membered, especially 5- to 8-membered saturated carbocycle which is optionally mono- or polysubstituted, e.g. mono-, di-, tri- or tetrasubstituted, by $C_1$-$C_4$-alkyl groups.

The compounds of the formula II are reacted with the hydrazone of the formula III in step i) of the process according to the invention typically at temperatures in the range from 0 to 180° C., especially in the range from 10 to 150° C.

For the reaction, the compounds II and III are preferably used in a ratio corresponding to the stoichiometry of the reaction, but it is also possible to deviate from the stoichiometry. Typically, the molar ratio of compound II to compound III is in the range from 1.5:1 to 1:1.5, frequently in the range from 1.2:1 to 1:1.2 and especially in the range from 1.1:1 to 1:1.1.

Typically, the reaction in step i) is effected in an inert organic solvent. Examples of inert organic solvents are especially aprotic organic solvents such as aromatic hydrocarbons and halohydrocarbons, for example benzene, toluene, xylenes, cumene, chlorobenzene and tert-butylbenzene, cyclic or acyclic ethers such as diethyl ether, diisopropyl ether, tert-butyl methyl ether (MTBE), tert-butyl ethyl ether, tetrahydrofuran (THF) or dioxane, nitriles such as acetonitrile and propionitrile, aliphatic halohydrocarbons such as dichloromethane, dichloroethane, trichloromethane and mixtures thereof. Preference is given to working under essentially anhydrous conditions in step i), i.e. the water content in the solution is below 1%, especially below 0.1%, based on the total weight of the solvent.

For the reaction of the compounds of the formula II with hydrazones of the formula III, the procedure will generally be to combine the compound of the formula II, preferably in the form of a solution in one of the aforementioned inert organic solvents, with the hydrazone III, which is preferably likewise used in the form of a solution in one of the aforementioned inert organic solvents. In this case, the hydrazone III can be initially charged as a solution in an organic solvent and the compound II can be added, preferably as a solution. Alternatively, the compound II can be initially charged as a solution in an organic solvent and the hydrazone can be added, preferably as a solution. The hydrazone III and the compound II can be combined in the abovementioned temperature ranges.

The procedure will frequently be that the compounds II and III are combined at temperatures in the range from 0 to 50° C., especially from 10 to 50° C., and then the reaction mixture is heated to the desired temperature. The reaction time is typically in the range from 1 h to 15 h.

In this way, the compound of the formula VI is obtained, and can be isolated from the reaction mixture. Alternatively, the reaction mixture can also be supplied to the reaction in step ii) of the process according to the invention without isolating the compound VI. A method without isolation of the intermediate compound VI is advantageous, since yield losses, as occur, for example, in the removal of the intermediate compound in the solid state by filtration (for example losses in the mother liquor), are reduced or avoided in this way. In these cases, a portion of the organic solvent used in step i) can optionally be removed and optionally replaced with another solvent. A method without isolation of the intermediate compound VI is especially also advantageous when the Y group in the compound II used is $[NR^{y2}R^{y3}]^+Z^-$.

According to the invention, the reaction is effected in the presence of an acid, especially of a Brønsted acid. Preferred acids have a pKa of not more than 4, especially not more than 3 or not more than 2 (in dilute (e.g. 0.01 M) aqueous solution at 25° C.). Preferred acids are hydrohalic acids such as HF, HCl and HBr, especially in the form of their aqueous solutions, sulfuric acid, phosphoric acid, $HBF_4$, and organic sulfonic acids, for example aromatic sulfonic acids of the formula Ar—$SO_3H$ in which Ar is optionally substituted phenyl, such as benzylsulfonic acid and p-toluenesulfonic acid, and also aliphatic sulfonic acids such as methanesulfonic acid, ethanesulfonic acid and trifluoromethanesulfonic acid. Likewise suitable are aliphatic and aromatic carboxylic acids such as formic acid, chloroacetic acid, dichloroacetic acid, trichloroacetic acid, trifluoroacetic acid, salicylic acid and 2-chlorobenzoic acid. It will be appreciated that mixtures of the aforementioned acids are also suitable.

For the reaction in step ii), catalytic amounts of acid are generally sufficient. The acid can, however, also be used in a stoichiometric or superstoichiometric amount. In general, the acid is used in an amount of from 0.01 to 10 mol and especially in the amount of from 0.02 to 5 mol per mol of compound VI, or, in the case of in situ preparation of the compound VI, in an amount of from 0.01 to 10 mol and especially in an amount of from 0.02 to 2 mol per mol of compound II.

According to the invention, the reaction in step ii) of the process according to the invention is effected in the presence of water. It is assumed that the water leads to the cleavage of the hydrazone group in the compound of the formula VI formed in step I to form the compound VIa (shown with Y=O), which is then cyclized to the pyrazole. When Y=O, the process according to the invention can be illustrated by the following scheme 1:

Scheme 1:

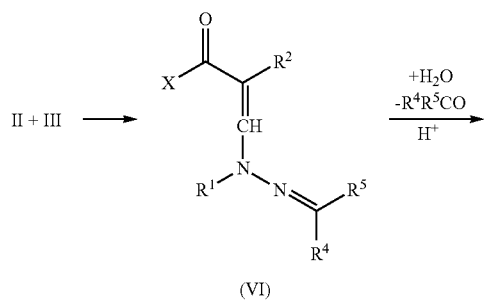

(VI)

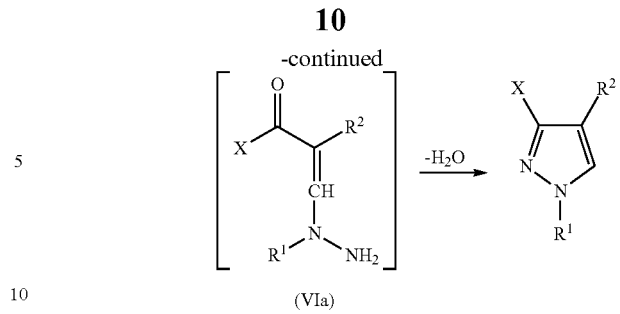

(VIa)

As is evident from the scheme, in the case that Y=O, even the presence of catalytic amounts of water is sufficient for the reaction, since water is formed in the reaction. Water can also be used in a stoichiometric or superstoichiometric amount. In general, water is used in an amount of from 0.001 to 50 mol and especially in an amount of from 0.01 to 20 mol per mol of compound VI, or, in the case of in situ preparation of the compound VI, in an amount of from 0.001 to 50 mol and especially in an amount of from 0.01 to 20 mol per mol of compound II.

It is assumed that the reaction of compound II in which Y is $NR^{y1}$ or $[NR^{y2}R^{y3}]^+Z^-$ with the hydrazone III and the subsequent cyclization to the pyrazole compound I proceeds in an analogous manner, although, in contrast to the variant where Y=O, at least stoichiometric amounts of water are required for a full conversion in the cyclization. Accordingly, in this case, the water is used typically in an amount of from 1 to 50 mol and especially in an amount of from 1.1 to 20 mol per mol of compound VI, or, in the case of in situ preparation of the compound VI, in an amount of from 1 to 50 mol and especially in an amount of from 1.1 to 20 mol per mol of compound II.

Typically, the reaction in step ii) is effected in the presence of an organic solvent or solvent mixture. Suitable organic solvents for the reaction in step ii) are protic polar solvents, for example aliphatic alcohols having preferably from 1 to 4 carbon atoms, such as methanol, ethanol, n-propanol, isopropanol, n-butanol, isobutanol or tert-butanol, or carboxylic acids such as acetic acid, aromatic hydrocarbons such as benzene, toluene, xylenes, cumene, chlorobenzene, nitrobenzene or tert-butylbenzene, aprotic polar solvents, for example cyclic or acyclic ethers such as diethyl ether, diisopropyl ether, tert-butyl methyl ether (MTBE), tert-butyl ethyl ether, tetrahydrofuran (THF) or dioxane, cyclic or acyclic amides such as dimethylformamide, dimethylacetamide, N-methylpyrrolidone or tetramethylurea, or aliphatic nitriles such as acetonitrile or propionitrile, and mixtures of the aforementioned solvents.

For the reaction in step ii), the procedure is generally to initially charge the compound of the formula VI prepared in step i) of the process according to the invention or the reaction mixture obtained in step i), optionally after a partial or full exchange of the solvent used in step i), in a suitable organic solvent and to add acid and water thereto. It is possible to introduce the water required for the reaction via the organic solvent. It is likewise possible to introduce the water required for the reaction via acid, for example in the form of an aqueous solution of the acid or in the form of a hydrate of the acid.

The reaction in step ii) of the process according to the invention is effected typically at temperatures in the range from 0 to 150° C., especially in the range from 20 to 110° C. The reaction time is typically in the range from 0.1 h to 15 h.

In step ii), the desired 1,3-pyrazole compound I is obtained in high yield at high selectivity, i.e. with a very low or undetectable proportion of undesired 1,5-isomer I'. For instance, the molar ratio of 1,3-isomer of the formula I to 1,5-isomer of the formula I' is generally at least 20:1, frequently at least 50:1, in particular at least 80:1 and especially at least 100:1.

The desired 1,3-pyrazole compound I can be isolated from the reaction mixture by customary methods, by means of precipitation, crystallization or distillation, or be processed further to conversion products in the form of the reaction mixture.

The compounds of the formula II used in the process according to the invention are known, for example, from the prior art cited at the outset or can be prepared in analogy to the methods described there.

Compounds of the formula II in which Y is oxygen and $R^3$ is an $OR^{3a}$ group are known, for example, from U.S. Pat. No. 5,498,624, JACS, 73, 3684, WO 92/12970, Chem. Ber. 1982, 115, 2766, Journal of Medicinal Chemistry, 2000, Vol. 43, No. 21 and the prior applications PCT/EP2007/061833 and EP 07109463.5, or can be prepared in analogy to the processes described there, for example by reacting acrylic compounds of the formula IX ($R^2$=CN or $CO_2R^{2a}$) with acyl halides (Q=halogen) or acyl anhydrides (Q=OC(O)X) of the formula X according to the following scheme 2a, or by reacting β-keto esters of the formula XI ($R^2$=$CO_2R^{2a}$) or β-keto nitriles XI ($R^2$=CN) with orthoformic esters of the formula XII according to the following scheme 2b.

Scheme 2a

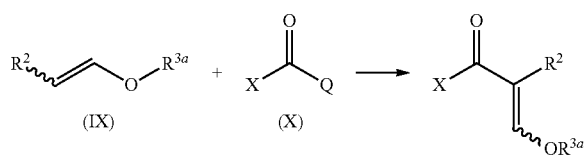

(IX)  (X)

Scheme 2b

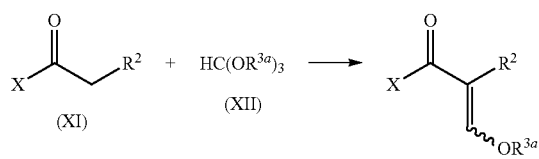

(XI)  (XII)

In schemes 2a and 2b, the variables $R^2$, $R^{3a}$ and X are each as defined above. Q is especially fluorine, chlorine or an OC(O)X radical in which X has one of the definitions given above.

Compounds of the formula II in which Y is oxygen and $R^3$ is an $NR^{3b}R^{3c}$ group are known, for example, from WO 03/051820, WO 2005/042468 and the prior applications PCT/EP2007/064390, EP 08155612.8 and EP 08155611.0 or can be prepared in analogy to the processes described there. Compounds of the formula II where $R^2$=CN or $CO_2R^{2a}$ can be prepared, for example, by reacting corresponding 3-aminoacrylic compounds XIII with the acyl compounds of the formula X described in scheme 2 by the reaction shown in scheme 3.

Scheme 3

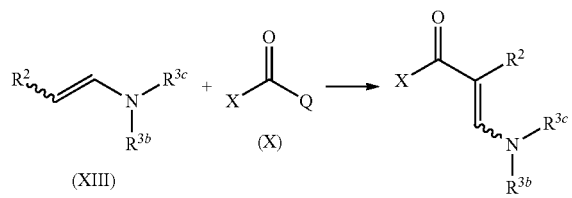

(XIII)  (X)

Compounds of the formula II in which Y is an $[NR^{y1}R^{y2}]Z^-$ group (compounds IIb) can be prepared, for example, by the processes described in WO 2008/022777 and the prior application EP 07110397.2. According to these, II in which Y is an $[NR^{y1}R^{y2}]Z^-$ group are prepared typically by reacting α,α-difluoroamines of the formula XIV with an olefinic compound of the formula XV in the presence of a Lewis acid such as $MgF_2$, $BF_3$, $BCl_3$, $AlCl_3$, $AlF_3$, $ZnCl_2$, $PF_5$, $SbF_5$, $BiCl_3$, $GaCl_3$, $SnCl_4$, or $SiCl_4$ by the process shown in scheme 4.

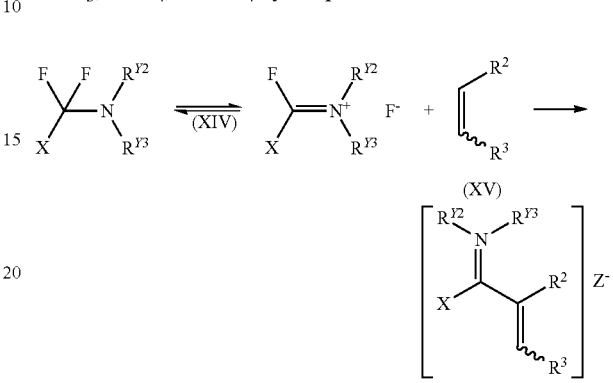

In this context, it has been found to be useful not to isolate the iminium compound IIb obtained by reaction of XIV with XV but rather to use the reaction mixture obtained, optionally after removal of a portion of the solvent, in the reaction with the hydrazone of the formula III. For details of the preparation of the compound IIb, reference is made especially to the disclosure of WO 2008/022777 and of the prior application WO 2008/152138 (formerly EP 07110397.2), which are hereby incorporated by reference.

The hydrazone compounds of the formula III used in the process according to the invention are known or can be prepared in a manner known per se by reacting a carbonyl compound of the formula IV with a substituted hydrazine compound of the formula V.

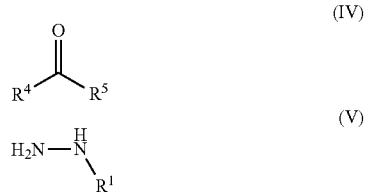

In the formulae IV and V, $R^1$, $R^4$ and $R^5$ are each as defined for formula III and VI. The compounds IV and V can be converted to the hydrazone III in a manner known per se.

The carbonyl compound IV is reacted with the hydrazine compound V typically at temperatures in the range from 10 to 180° C., especially in the range from 20 to 150° C.

For the reaction, the compounds IV and V are preferably used in a ratio corresponding to the stoichiometry of the reaction, but it is also possible to deviate from the stoichiometry. Typically, the molar ratio of compound IV to compound V is in the range from 1.5:1 to 1:1.5, frequently in the range from 1.2:1 to 1:1.2 and especially in the range from 1.1:1 to 1:1.1.

Typically, IV is reacted with V in an inert organic solvent. Examples of inert organic solvents are especially aprotic organic solvents such as aromatic hydrocarbons and halohydrocarbons, for example benzene, toluene, xylenes, cumene, chlorobenzene and tert-butylbenzene, cyclic or acyclic ethers such as diethyl ether, diisopropyl ether, tert-butyl methyl ether (MTBE), tert-butyl ethyl ether, tetrahydrofuran (THF) or dioxane, nitriles such as acetonitrile and propionitrile, aliphatic halohydrocarbons such as dichloromethane, dichloroethane, trichloromethane and mixtures thereof.

For the reaction of the compounds of the formula IV with the hydrazine compound of the formula V, the procedure will generally be to combine the compound of the formula IV, preferably in the form of a solution in one of the aforementioned inert organic solvents, with the hydrazine compound V, preferably as a solution in water. The compounds IV and V can be combined within the abovementioned temperature ranges. Frequently, the procedure will be such that the compounds IV and V are combined at temperatures in the range from 0 to 50° C., especially from 10 to 50° C., and then the reaction mixture is heated to the desired temperature. The reaction time is typically in the range from 0.5 h to 8 h.

In general, it has been found to be advantageous to remove the water formed in the reaction or the water introduced by virtue of use of an aqueous solution of the hydrazine V, for example by distillation, water separation, by means of an azeotroping agent, by phase separation, another kind of drying or a combination of these measures.

The hydrazone can be isolated from the reaction mixture obtained by reaction of IV with V or be used as the reaction mixture in the next stage, i.e. in step I of the process according to the invention.

The present invention further relates to a process for preparing a compound of the general formula Ia

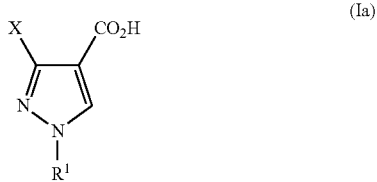

in which X and $R^1$ are each as defined above, comprising the following steps
a) providing a pyrazole compound of the formula I by a process according to the process described here,
b) converting the compound I to a 1,3-substituted pyrazolecarboxylic acid of the formula Ia.

The conversion is effected typically by hydrolysis. Accordingly, a preferred embodiment of the invention relates to a process comprising the following steps:
a) the provision of a compound of the formula I by the process according to the invention as described and
b) hydrolysis of the compound I to form a 1,3-substituted pyrazol-4-ylcarboxylic acid of the formula Ia.

The hydrolysis can be carried out under acid catalysis or by basic means or otherwise. The compound I can be used as such, i.e. after isolation. However, it is also possible to use the reaction mixture obtained in step a) for the hydrolysis without further purification, optionally after removal of volatile constituents such as solvents.

For the basic hydrolysis of the compound I, the compound of the formula I will typically be treated with an alkali metal hydroxide such as sodium hydroxide, potassium hydroxide or lithium hydroxide, preferably with an aqueous alkali metal hydroxide solution, especially an aqueous NaOH solution or an aqueous KOH solution, until complete hydrolysis of the ester, preferably while heating.

In the basic hydrolysis, the molar ratio of compound of the formula I to base is typically in the range from 1.2:1 to 1:10 and is especially approximately equimolar (i.e. is in the range from 1.1:1 to 1:1.5), but a relatively large excess of base, for example up to 5 mol per mol of compound I, may also be advantageous.

Typically, the basic hydrolysis is effected in a diluent or solvent. Suitable diluents or solvents are, as well as water, also organic solvents which are stable toward alkali, and mixtures thereof with water. Examples of alkali-stable organic solvents are especially the aforementioned $C_1$-$C_4$-alkanols and the aforementioned acyclic ethers and the cyclic ethers. Preference is given to performing the hydrolysis in the aqueous phase, i.e. in water or a mixture of water with one of the aforementioned organic solvents, in which case the content of organic solvent in the aqueous phase typically does not exceed generally 30% by volume, based on the total amount of water and organic solvent.

Preference is given to performing the basic hydrolysis at temperatures of from 20 to 100° C. In general, the upper temperature limit is the boiling point of the solvent used when the reaction is conducted at ambient pressure. A reaction temperature of 100° C. and especially 90° C. will preferably not be exceeded. In a preferred embodiment, however, the basic hydrolysis is performed at a temperature below the boiling point of the alcohol component, for example at temperatures in the range from 40 to <80° C., especially in the range from 50 to 75° C., especially when proceeding from a compound of the general formula I in which $R^1$ is methyl or ethyl. Higher temperatures are, however, likewise possible. For instance, in another embodiment of the basic hydrolysis, a temperature above the boiling point of the alcohol component of the ester is employed. For example, the hydrolysis will then be carried out preferably at a temperature of at least 80° C., for example in the range from 80 to 100° C., e.g. when proceeding from a compound of the general formula I in which $R^1$ is ethyl. The reaction time depends here on the reaction temperature, the concentration and the stability of the particular ester bond. In general, the reaction conditions are selected such that the reaction time is in the range from 1 to 12 h, especially in the range from 2 to 8 h.

In a particularly preferred embodiment of the invention, for the preparation of a compound of the general formula Ia, the pyrazole compound I obtained in step a), in the case that $R^2$ is $CO_2R^{2a}$ or CN, without intermediate isolation, advantageously together with the organic solvent, will be reacted with the aqueous alkali metal hydroxide solution. The alkali metal salt of the pyrazolecarboxylic acid Ia formed is obtained as an aqueous phase in addition to the organic phase, which can be removed by phase separation. In this way, the carbonyl compound IV ($R^4R^5C=O$) released again in the reaction of the compounds II and III in step ii), especially when $R^4$ is optionally substituted phenyl, can be removed with the organic phase. Recycling of the carbonyl compound IV into the reaction process for hydrazone formation (optionally after preceding further workup, for example by distillation) is thus possible. Recycling of the organic solvent used can also be undertaken. The aqueous phase obtained in the phase separation comprises the alkali metal salt of the 1,3-substituted acid Ia generally in dissolved form and. The salt can then be converted to the free acid Ia by acidifying the solution as described above. In general, the acid Ia is obtained as a solid and can be isolated by filtration and optionally dried. In this procedure, the 1,3-substituted pyrazolecarboxylic acid is obtained in high purity and with very good yield. The yield, based on the compound II used, is generally at least 80% and especially at least 85%.

The acidic hydrolysis of the compound I can be carried out in analogy to known acidic ester hydrolyses, i.e. in the presence of catalytic or stoichiometric amounts of an acid and water (see, for example, J. March, Advanced Organic Chemistry, 2nd Ed., 334-338, McGraw-Hill, 1977 and literature cited there). Frequently, the reaction will be performed in a mixture of water and aprotic organic solvent, for example an ether as specified above. Examples of acids are hydrohalic acids, sulfuric acid, organic sulfonic acids such as p-toluenesulfonic acid, methanesulfonic acid, phosphoric acid and acidic anion exchangers, and the like.

Suitable hydrolysis catalysts are also alkali metal iodides such as lithium iodide, trimethyliodosilane or mixtures of trimethylchlorosilane with alkali metal iodides such as lithium, sodium or potassium iodide.

The acid Ia is then isolated by customary separation processes, for example precipitation by adjusting the pH or extraction.

The pyrazole compounds of the formula I, especially the pyrazolecarboxylic acids of the formula Ia, are valuable intermediates in the preparation of active ingredients which have a 1,3-substituted pyrazole radical, especially in the preparation of active fungicidal ingredients of the formula VII described below:

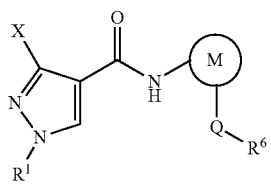
(VII)

in which $R^1$ and X each have one of the definitions given in claim 1;

M is thienyl or phenyl which may bear a halogen substituent;

Q is a direct bond, cyclopropylene, a fused bicyclo[2.2.1]heptane or bicyclo[2.2.1]heptene ring; and $R^6$ is hydrogen, halogen, $C_1$-$C_4$-alkyl, $C_1$-$C_4$-haloalkoxy, mono- to trisubstituted phenyl, where the substituents are each independently selected from halogen and trifluoromethylthio, or cyclopropyl.

Accordingly, the present invention also relates to a process for preparing a compound of the formula VII, comprising the following steps:

a) providing a pyrazole compound of the formula I by the process according to the invention;

b) converting the compound I to a 1,3-substituted pyrazolecarboxylic acid of the formula Ia,

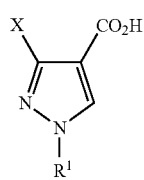
(Ia)

in which X and $R^1$ are each as defined above;

c) optionally converting the compound Ia to its acid halide; and d) reacting the compound of the formula Ia or its acid halide with an amine compound of the formula VIII,

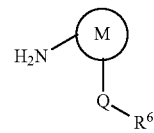
(VIII)

in which M, Q and $R^6$ are each as defined for formula VII.

Suitable methods for preparing carboxylic acids and reaction of carboxylic acids or carbonyl halides with aromatic amines are known to those skilled in the art, for example from the prior art cited at the outset (see U.S. Pat. No. 5,498,624, EP 545099 A1, DE 19531813 A1, EP 589301 A1, DE 19840322 A1, WO 92/12970, WO 03/066610, WO 2006/024389, WO 2007/003603, WO 2007/006806) and from J. March, Advanced Organic Chemistry, 3rd ed. J. Wiley and Sons, New York 1985, p. 370-386 and literature cited there, and also Organikum, 21st edition, Wiley-VCH, Weinheim 2001, p. 481-484 and literature cited there, and can be applied to the inventive preparation of the compounds VII by reacting the pyrazolecarboxylic acid Ia or acid halide thereof with the aniline compound VIII in an analogous manner.

Frequently, the procedure will be first to convert the pyrazolecarboxylic acid of the formula Ia to its acid halide, for example its acid chloride, and then to react the acid halide with the amine compound of the formula VIII. The pyrazolecarboxylic acid can be converted to its acid chloride in analogy to standard processes of organic chemistry, for example by reaction with thionyl chloride. The subsequent reaction of the acid halide with the amine compound VIII is effected typically in the presence of an auxiliary base, for example a tertiary amine. Alternatively, the pyrazolecarboxylic acid of the formula Ia can also be reacted directly with the amine compound VIII, preferably in the presence of a dehydrating agent such as 1,1'-carbonyldiimidazole, bis(2-oxo-3-oxazolidinyl)phosphoryl chloride, N,N'-dicyclohexylcarbodiimide or N-(3-dimethylamino-propyl)-N'-ethylcarbodiimide in the presence of an auxiliary base, for example a tertiary amine, to give the compound VII, as described, for example, in prior patent application PCT/EP2007/064390, whose disclosure is hereby explicitly incorporated by reference.

Examples of compounds of the formula VII which can be prepared by processes described here are:

N-(2-bicyclopropyl-2-yl-phenyl)-3-difluoromethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-trifluorobiphenyl-2-yl)-3-(chlorodifluoromethyl)-1-methylpyrazol-4-yl-carboxamide, N-(3',4',5'-trifluorobiphenyl-2-yl)-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-yl-carboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-(chlorodifluoromethyl)-1-methylpyrazol4-yl-carboxamide,
N-(2',4',5'-trifluorobiphenyl-2-yl)-1-methyl-3-trifluoromethylpyrazol4-ylcarboxamide,
N-(3',4'-dichloro-3-fluorobiphenyl-2-yl)-1-methyl-3-trifluoromethyl-1H-pyrazol-4-yl-carboxamide,
N-(3',4'-dichloro-3-fluorobiphenyl-2-yl)-1-methyl-3-difluoromethyl-1H-pyrazol-4-yl-carboxamide,
N-(3',4'-difluoro-3-fluorobiphenyl-2-yl)-1-methyl-3-trifluoromethyl-1H-pyrazole-4-carboxamide,
N-(3',4'-difluoro-3-fluorobiphenyl-2-yl)-1-methyl-3-difluoromethyl-1H-pyrazol-4-yl-carboxamide,
N-(3'-chloro-4'-fluoro-3-fluorobiphenyl-2-yl)-1-methyl-3-difluoromethyl-1H-pyrazol-4-yl-carboxamide,
N-(3',4'-dichloro-4-fluorobiphenyl-2-yl)-1-methyl-3-trifluoromethyl-1H-pyrazol-4-yl-carboxamide,
N-(3',4'-difluoro-4-fluorobiphenyl-2-yl)-1-methyl-3-trifluoromethyl-1H-pyrazol-4-yl-carboxamide,
N-(3',4'-dichloro-4-fluorobiphenyl-2-yl)-1-methyl-3-difluoromethyl-1H-pyrazol-4-yl-carboxamide,
N-(3',4'-difluoro-4-fluorobiphenyl-2-yl)-1-methyl-3-difluoromethyl-1H-pyrazol-4-yl-carboxamide,
N-(3'-chloro-4'-fluoro-4-fluorobiphenyl-2-yl)-1-methyl-3-difluoromethyl-1H-pyrazol-4-yl-carboxamide,
N-(3',4'-dichloro-5-fluorobiphenyl-2-yl)-1-methyl-3-trifluoromethyl-1H-pyrazol-4-yl-carboxamide,
N-(3',4'-difluoro-5-fluorobiphenyl-2-yl)-1-methyl-3-trifluoromethyl-1H-pyrazol-4-yl-carboxamide,
N-(3',4'-dichloro-5-fluorobiphenyl-2-yl)-1-methyl-3-difluoromethyl-1H-pyrazol-4-yl-carboxamide,
N-(3',4'-difluoro-5-fluorobiphenyl-2-yl)-1-methyl-3-difluoromethyl-1H-pyrazol-4-yl-carboxamide,
N-(3',4'-dichloro-5-fluorobiphenyl-2-yl)-1,3-dimethyl-1H-pyrazol-4-ylcarboxamide,
N-(3'-chloro-4'-fluoro-5-fluorobiphenyl-2-yl)-1-methyl-3-difluoromethyl-1H-pyrazol-4-yl-carboxamide,
N-(4'-fluoro-4-fluorobiphenyl-2-yl)-1-methyl-3-trifluoromethyl-1H-pyrazol-4-yl-carboxamide,
N-(4'-fluoro-5-fluorobiphenyl-2-yl)-1-methyl-3-trifluoromethyl-1H-pyrazol-4-yl-carboxamide,
N-(4'-chloro-5-fluorobiphenyl-2-yl)-1-methyl-3-trifluoromethyl-1H-pyrazol-4-yl-carboxamide,
N-(4'-methyl-5-fluorobiphenyl-2-yl)-1-methyl-3-trifluoromethyl-1H-pyrazol-4-yl-carboxamide,
N-(4'-fluoro-5-fluorobiphenyl-2-yl)-1,3-dimethyl-1H-pyrazol-4-ylcarboxamide,
N-(4'-chloro-5-fluorobiphenyl-2-yl)-1,3-dimethyl-1H-pyrazol-4-ylcarboxamide,
N-(4'-methyl-5-fluorobiphenyl-2-yl)-1,3-dimethyl-1H-pyrazol-4-ylcarboxamide,
N-(4'-fluoro-6-fluorobiphenyl-2-yl)-1-methyl-3-trifluoromethyl-1H-pyrazol-4-yl-carboxamide,
N-[2-(1,1,2,3,3,3-hexafluoropropoxy)-phenyl]-3-difluoromethyl-1-methyl-1H-pyrazol-4-ylcarboxamide,
N-[4''-(trifluoromethylthio)biphenyl-2-yl]-3-difluoromethyl-1-methyl-1H-pyrazol-4-ylcarboxamide,
N-[4'-(trifluoromethylthio)biphenyl-2-yl]-1-methyl-3-trifluoromethyl-1H-pyrazol-4-ylcarboxamide,
3-(difluoromethyl)-1-methyl-N-[1,2,3,4-tetrahydro-9-(1-methylethyl)-1,4-methanonaphthalen-5-yl]-1H-pyrazol-4-ylcarboxamide,
N-(3'-chloro-5-fluorobiphenyl-2-yl)-3-(difluoromethyl)-1-methylpyrazol-4-ylcarboxamide,
N-(4'-chloro-5-fluorobiphenyl-2-yl)-3-(difluoromethyl)-1-methylpyrazol-4-ylcarboxamide,
N-(4'-chlorobiphenyl-2-yl)-3-(difluoromethyl)-1-methylpyrazol-4-ylcarboxamide,
N-(4'-bromobiphenyl-2-yl)-3-(difluoromethyl)-1-methylpyrazol-4-ylcarboxamide,
N-(4'-iodobiphenyl-2-yl)-3-(difluoromethyl)-1-methylpyrazol-4-ylcarboxamide,
N-(3',5'-difluorobiphenyl-2-yl)-3-(difluoromethyl)-1-methylpyrazol-4-ylcarboxamide,
N-(2-chloro-4-fluorophenyl)-3-(difluoromethyl)-1-methylpyrazol-4-ylcarboxamide,
N-(2-bromo-4-fluorophenyl)-3-(difluoromethyl)-1-methylpyrazol-4-ylcarboxamide,
N-(2-iodo-4-fluorophenyl)-3-(difluoromethyl)-1-methylpyrazol-4-ylcarboxamide and
N-[2-(1,3-dimethylbutyl)phenyl]-1,3-dimethyl-5-fluoro-1H-pyrazol-4-ylcarboxamide.

The examples which follow serve to further illustrate the invention.

PREPARATION EXAMPLE 1

Benzaldehyde Methylhydrazone 18.4 g (0.4 mol) of methylhydrazine were initially charged in 248.7 g of diethyl ether. At 22-26° C., 42.4 g (0.4 mol) of benzaldehyde were added dropwise within 1.75 hours. The reaction mixture was then stirred at reflux temperature for 5 hours. The residue obtained after the solvent had been distilled off was taken up in diethyl ether and the solution was dried over sodium sulfate. After drying, the solution was concentrated under reduced pressure and the residue obtained was distilled at 78° C./0.5-1 mbar.

$^1$H NMR (500 MHz, CDCl$_3$): δ (ppm)=2.85 (s, 3H), 5.55 (br., 1H), 7.2 (1H), 7.3 (2H), 7.45 (1H), 7.55 (2H)

In analogy to the method of preparation example 1, the following hydrazones were prepared:

| Preparation ex. | Hydrazone |
| --- | --- |
| 2 | o-chlorobenzylidene methylhydrazone |
| 3 | p-methoxybenzylidene methylhydrazone |
| 4 | p-methylbenzylidene methylhydrazone |
| 5 | o-nitrobenzylidene methylhydrazone |
| 6 | p-nitrobenzylidene methylhydrazone |
| 7 | cyclohexylidene methylhydrazone |

EXAMPLE 1

Preparation of Ethyl 3-difluoromethyl-1-methyl-1H-pyrazole-4-carboxylate and Subsequent Hydrolysis to 3-difluoromethyl-1-methyl-1H-pyrazole-4-carboxylic Acid 1.1. Ethyl 4,4-difluoro-2-[1-{N-methyl-N'-[1-phenylmethylidene]hydrazino}-methylidene]-3-oxobutyrate 13.8 g (0.1 mol) of benzaldehyde methylhydrazone and 62.2 g of toluene were admixed with 23.7 g (0.1 mol) of ethyl 2-ethoxymethylene-4,4-difluoro-3-oxo-butyrate, as a result of which the internal temperature rose to 35° C. The reaction mixture was stirred at reflux temperature for 1.25 hours and then stirred at 25° C. for 15 hours. The precipitated solid was filtered off with a suction filter and washed twice with 25 m; each time of toluene. After drying at 40-50° C. under reduced pressure, 23 g of product were obtained.

Purity by HPLC: 99.2 area %

MS: Monoisotopic relative molecular mass m/z=310

$^1$H NMR (500 MHz, DMSO-d6): E/Z isomer mixture (approx. 2:1) based on the C=C double bond: δ (ppm)=1.07 and 2.2 (3H), 3.55 and 3.62 (3H), 4.08-4.2 (2H), 6.15 and 6.7 (t, 1H, —CHF$_2$—), 7.4-7.75 (5H), 7.93 (1H), 8.05 and 8.13 (1H)

$^{13}$C NMR: 190.1, 181.4, 166.6, 164.7, 148.9, 146.1, 145.5, 133.9, 130.3, 128.8, 127.7, 110.4, 108.5, 107.0, 99.23, 60.46, 59.66, 39.43, 13.81.

1.2.
3-Difluoromethyl-1-methyl-1H-pyrazole-4-carboxylic acid 20 g (0.065 mol) of ethyl 4,4-difluoro-2-[1-{N-methyl-N'-[1-phenylmethylidene]hydrazino}methylidene]-3-oxobutyrate from step 1.1. was initially charged together with 252.7 g of ethanol under a nitrogen atmosphere at 25° C. Within 5 minutes, 14.8 g (0.13 mol) of hydrochloric acid (32%) were added dropwise. The suspension was heated to 45° C. and stirred at ambient temperature for a further 30 minutes. Thereafter, a clear yellow solution was present. The solution (285 g) comprised 4.12% by weight of the desired ethyl 3-difluoromethyl-1-methyl-1H-pyrazole-4-carboxylate (HPLC analysis, quantification with internal standard), corresponding to a yield of 89.2%. The proportion of the isomeric ethyl 5-difluoromethyl-1-methyl-1H-pyrazole-4-carboxylate was only 0.05% by weight (isomer ratio approx. 82:1).

At 25-27° C., 104 g (0.26 mol) of 10% sodium hydroxide solution were then metered in within 5 minutes and rinsed in with 50 ml of water. The reaction mixture was stirred at 60° C. for 2.5 hours. At 58° C./370 mbar, 320 g of solvent (ethanol/water) were distilled off, which left a biphasic distillation residue. After dilution with 100 ml of toluene, the phases were separated. The toluenic upper phase comprised mainly the benzaldehyde released. The lower aqueous phase comprised, as the main component, the sodium salt of the desired 3-difluoromethyl-1-methyl-1H-pyrazole-4-carboxylic acid. The aqueous phase removed was acidified with 29.7 g (0.26 mol) of concentrated hydrochloric acid (pH<2), which precipitated the title compound. After filtration, 18.2 g of the moist 3-difluoromethyl-1-methyl-1H-pyrazole-4-carboxylic acid were obtained. HPLC analysis (quantification with external standard) showed a content of 52.6% by weight, corresponding to a yield of 83%, based on the ethyl 4,4-difluoro-2-[1-{N-methyl-N'-[1-phenylmethylidene]hydrazino}methylidene]-3-oxobutyrate used for the reaction.

EXAMPLE 2

Preparation of Ethyl 3-difluoromethyl-1-methyl-1H-pyrazole-4-carboxylate with a Catalytic Amount of P-Toluenesulfonic Acid and Subsequent Hydrolysis to Give 3-difluoromethyl-1-methyl-1H-pyrazole-4-carboxylic Acid 62 g (0.2 mol) of ethyl 4,4-difluoro-2-[1-{N-methyl-N'-[1-phenylmethylidene]hydrazino}methylidene]-3-oxobutyrate (prepared analogously to example 1, step 1.1., purity 99.1 area %) were initially charged together with 150 g of ethanol at 15° C. under a nitrogen atmosphere. 1.6 g (0.0083 mol) of p-toluenesulfonic acid monohydrate were added and the mixture was stirred at 25° C. for 15 hours and at 50° C. for 1 hour. The solution comprised 14.9% by weight of the desired ethyl 3-difluoromethyl-1-methyl-1H-pyrazole-4-carboxylate (HPLC analysis, quantification with external standard). The proportion of the isomeric ethyl 5-difluoromethyl-1-methyl-1H-pyrazole-4-carboxylate is only 0.069% by weight (corresponding to an isomer ratio of >200:1).

168.3 g (0.3 mol) of 10% potassium hydroxide solution were then metered in and the reaction mixture was stirred at 60° C. for 3 hours. After cooling to 25° C., the phases were separated. The toluenic upper phase comprised mainly the benzaldehyde released. The lower aqueous phase comprised, as the main component, the potassium salt of the desired 3-difluoromethyl-1-methyl-1H-pyrazole-4-carboxylic acid. The toluene phase was washed twice more with 50 g each time of water. The combined water phases were acidified at 55° C. with 66 g (0.579 mol) of concentrated hydrochloric acid (32%) (pH<2), which precipitated the desired title compound. The solids were filtered off at 3° C. and washed with 132 g of cold water. After drying (60° C., 20 mbar), 32.1 g of 3-difluoromethyl-1-methyl-1H-pyrazole-4-carboxylic acid were obtained in a purity of 99% by weight. The yield based on the molar amount of methylhydrazine or ethyl 2-ethoxymethylene-4,4-difluoro-3-oxobutyrate used was 90.3%. The undesired 1,5-isomer is no longer detectable.

EXAMPLE 3

Preparation of 3-difluoromethyl-1-methyl-1H-pyrazole-4-carboxylic Acid from Benzaldehyde, Methylhydrazine and Ethyl Ethoxymethylene-4,4-difluoro-3-oxobutyrate without Isolation/Purification of the Intermediates (One-Pot Method)

9.4 g (0.2 mol) of methylhydrazine (98% pure) were initially charged in 150.2 g of toluene. At 22-26° C., 21.4 g (0.2 mol) of benzaldehyde were added dropwise within 10 minutes. Subsequently, the mixture was heated to 40° C. and the progress of the reaction was monitored by means of GC analysis. After 8 hours, benzaldehyde was no longer detectable. The water phase was removed. A sufficient amount of solvent was distilled off from the toluene phase, comprising the hydrazine, at 40° C. and under reduced pressure, that the solution became clear (removal of residual water).

The remaining solution (91.1 g) was cooled to 3° C. At this temperature, 45.7 g (0.2 mol) of ethyl 2-ethoxymethylene-4,4-difluoro-3-oxobutyrate (97.1% pure) were added dropwise as a solution in 60 g of toluene. After heating to 25° C., the mixture was stirred at this temperature for a further 15 hours. This formed a pale yellow suspension (precipitated ethyl 4,4-difluoro-2-[1-{N-methyl-N'-[1-phenylmethylidene]hydrazino}-methylidene]-3-oxobutyrate).

1.7 g of p-toluenesulfonic acid monohydrate (0.009 mol) were added to the suspension which was stirred at 70° C. for 1 hour, which formed a clear solution. After HPLC analysis (quantification with external standard), 15.2% by weight of the desired ethyl 3-difluoromethyl-1-methyl-1H-pyrazole-4-carboxylate and only 0.164% by weight of the undesired ethyl 5-difluoromethyl-1-methyl-1H-pyrazole-4-carboxylate were present (corresponding to an isomer ratio of >92:1).

168.3 g of 10% potassium hydroxide solution (0.3 mol) were added to the solution and the mixture was stirred at 60° C. for 3 hours. After cooling to 25° C., the phases were separated. The toluenic upper phase comprised mainly the benzaldehyde released. The lower aqueous phase comprised, as the main component, the potassium salt of the desired 3-difluoromethyl-1-methyl-1H-pyrazole-4-carboxylic acid. The toluene phase was washed twice more with 50 g of water each time. The combined water phases were acidified at 55° C. with 66 g (0.579 mol) of conc. hydrochloric acid (32%) (pH<2), which precipitates the desired carboxylic acid. The solids were filtered off at 3° C. and washed with 132 g of cold water. After drying (60° C., 20 mbar), 30.6 g of 3-difluoromethyl-1-methyl-1H-pyrazole-4-carboxylic acid are obtained in a purity of 98.6% by weight: The yield based on the molar amount of methylhydrazine or ethyl 2-ethoxymethylene-4,4-difluoro-3-oxobutyrate used is 85.7%. The undesired carboxylic acid isomer is no longer present.

EXAMPLE 4

Preparation of 3-difluoromethyl-1-methyl-1H-pyrazole-4-carboxylic Acid from Acetone, Methylhydrazine and Ethyl Ethoxymethylene-4,4-difluoro-3-oxobutyrate without Isolation/Purification of the Intermediates (One-Pot Method)

11.5 g (0.245 mol) of methylhydrazine (98% pure) were initially charged in 150 g of toluene. At 0-5° C., 15.1 g (0.258 mol) of acetone were added dropwise within 10 minutes. The mixture was stirred at 5° C. for a further 1 hour. Toluene/water was then distilled off up to an internal temperature of 100° C. In this way, 163.1 g of a solution of acetone methylhydrazone in toluene were obtained.

A solution of 56.9 g (0.24 mol) of ethyl 2-ethoxymethylene-4,4-difluoro-3-oxobutyrate (93.7% pure) and 60° C. of toluene were metered at 23° C. into 163.1 g of acetone methylhydrazine solution within 10 minutes. The mixture was stirred at 3° C. for a further 1 h. At 40° C. under reduced pressure, 100 g of solvent were distilled off and 100 g of fresh toluene were metered in again. At 15° C., 2 g (0.01 mol) of p-toluenesulfonic acid monohydrate were added, which increased the internal temperature up to 35° C. After cooling to 25° C., the mixture was stirred at this temperature for another 1 hour. After HPLC analysis (quantification with external standard), 11.3% by weight of the desired ethyl 3-difluoromethyl-1-methyl-1H-pyrazole-4-carboxylate and only 0.064% by weight of the undesired ethyl 5-difluoromethyl-1-methyl-1H-pyrazole-4-carboxylate were present (corresponding to an isomer ratio of >175:1).

202 g of 10% potassium hydroxide solution (0.361 mol) were added to the solution and the mixture was stirred at 60° C. for 3 hours. After cooling to 25° C., the phases were separated. The toluenic upper phase comprised mainly the benzaldehyde released. The lower aqueous phase comprised, as the main component, the potassium salt of the title compound. The toluene phase was washed twice more with 50 g each time of water. The combined water phases were acidified at 55° C. with 80 g (0.7 mol) of concentrated hydrochloric acid (32%) (pH<2), which precipitated the desired pyrazole-carboxylic acid. The solids were filtered off at 3° C. and washed with 160 g of cold water. After the drying (60° C., 20 mbar), 34.6 g of 3-difluoromethyl-1-methyl-1H-pyrazole-4-carboxylic acid were obtained in a purity of 99% by weight. The yield based on the molar amount of ethyl 2-ethoxymethylene-4,4-difluoro-3-oxobutyrate used was 81%. The undesired 1,5-isomer was no longer detectable.

EXAMPLE 5

Preparation of methyl 3-difluoromethyl-1-methylpyrazole-4-carboxylate from 1,1,2,2-tetrafluoroethyldimethylamine, Methyl 3-methoxyacrylate and N-methyl-benzaldehyde Hydrazone To a solution of 96% pure 1,1,2,2-tetrafluoroethyldimethylamine (48.1 g, 318 mmol) in acetonitrile (97 g) under argon were added dropwise, at 25° C., 38.4 g (270 mmol) of $BF_3$ etherate. After the addition had ended, the mixture was heated to reflux (70° C.). At this temperature, a solution of 95% pure methyl 3-methoxyacrylate (33.1 g, 271 mmol) in acetonitrile (61 g) was added dropwise to the reaction mixture within 1 h. After stirring under reflux for 20 h, the reaction mixture was cooled to 25° C. and 99.8 g of a 38% solution of N-methyl-benzalde hydrazone in toluene (287 mmol) were added at 25° C. within 15 min. After a further stirring phase of 0.5 h, 10.4 g of a 50% by weight solution of water in acetonitrile (289 mmol) were added. 32.7 g (287 mmol) of 32% hydrochloric acid were then added and the mixture was heated to reflux with stirring for 3 h. Subsequently, the mixture was cooled to 25° C. and 100 ml of water were added. The organic phase was removed; the water phase was extracted once with 100 ml of methylene chloride. The combined organic phases were washed once with 100 ml of water. 391 g of organic phase were obtained. Gas chromatography analysis showed that the undesired 1,5-isomer (methyl 5-difluoromethyl-1-methylpyrazole-4-carboxylate) had been formed only in traces in addition to the methyl 3-difluoromethyl-1-methylpyrazole-4-carboxylate. The isomer ratio was 141:1. The organic phase was concentrated. 63.6 g of residue were obtained, which, as well as benzaldehyde, according to quantitative HPLC analysis, comprised 71.7% by weight of methyl 3-difluoromethyl-1-methylpyrazole-4-carboxylate. This corresponds to 89% yield based on methyl 3-methoxyacrylate. The benzaldehyde can be removed easily by fractional distillation or after hydrolysis of the title compound as described in examples 1 to 4.

EXAMPLE 6

Preparation of 3-difluoromethyl-1-methyl-1H-pyrazole-4-carboxylic Acid from Benzaldehyde, Aqueous Methylhydrazine Solution and ethyl ethoxymethylene-4,4-difluoro-3-oxobutyrate without Isolation/Purification of the Intermediates (One-Pot Method)

108.2 g (0.816 mol) of methylhydrazine solution (34.7% by weight of methylhydrazine in water) and 560 g of toluene were initially charged under a nitrogen atmosphere in a stirred vessel. At 25-40° C., 85.7 g (0.8 mol) of benzaldehyde (99%) were added dropwise within 10 minutes. The reaction mixture was stirred at 40° C. for 3 hours and at 60° C. for 3 hours. Subsequently, toluene/water was distilled off at 70° C./150 mbar, in the course of which the water of the condensed distillate was removed in a phase separator and the toluene phase was recycled into the reactor. After the water separation, 656 g of a clear solution of benzaldehyde methylhydrazone in toluene remained.

To this solution were added dropwise, at 20-30° C. within 1 hour, 189.5 g (0.8 mol) of ethyl 2-ethoxymethylene-4,4-difluoro-3-oxobutyrate (93.7% pure) as a solution in 189.5 g of toluene. The mixture was stirred at 25° C. for a further 18 hours. A suspension formed (precipitated ethyl 4,4-difluoro-2-[1-{N-methyl-N'-[1-phenyl-methylidene]hydrazino}methylidene]-3-oxobutyrate).

6.2 g of p-toluenesulfonic acid monohydrate (0.032 mol) were added at 10° C. to the suspension which was stirred at 50° C. for 1 hour, which formed a clear solution. According to HPLC analysis (quantification with external standard), the concentration of the desired ethyl 3-difluoromethyl-1-methyl-1H-pyrazole-4-carboxylate was 11.4% by weight.

672 g of 10% potassium hydroxide solution (1.2 mol) were added to the solution and the mixture was stirred at 60° C. for 3 hours. After cooling to 25° C., the phases were separated. The toluenic upper phase comprised mainly the benzaldehyde released. The lower aqueous phase comprised, as the main component, the potassium salt of the desired 3-difluoromethyl-1-methyl-1H-pyrazole-4-carboxylic acid. The toluene phase was washed twice more with 200 g each time of water. The combined water phases were acidified at 55° C. with 265 g (2.32 mol) of conc. hydrochloric acid (32%) (pH<2), which precipitated the desired pyrazolecarboxylic acid. The solids were filtered off at 3° C. and washed twice with 265 g each time of cold water. After the drying (60° C., 20 mbar), 121.8 g of 3-difluoromethyl-1-methyl-1H-pyrazole-4-carboxylic acid were obtained in a purity of 99.5% by weight. The yield based on the molar amount of benzaldehyde or ethyl 2-ethoxymethylene-4,4-difluoro-3-oxobutyrate used was 86.1%. The undesired carboxylic acid isomer was no longer detectable.

EXAMPLE 7

Preparation of 3-difluoromethyl-1-methyl-1H-pyrazole-4-carboxylic Acid from Benzaldehyde, Aqueous Methylhydrazine Solution and Ethyl Ethoxymethylene-4,4-difluoro-3-oxobutyrate without Isolation/Purification of the Intermediates (One-Pot Method)

368.3 g (2.78 mol) of methylhydrazine solution (34.7% by weight of methylhydrazine in water) and 1888 g of toluene were initially charged in a stirred vessel under a nitrogen atmosphere. The reaction mixture was heated to 40° C. At 40° C. to 60° C., 300.9 g (2.81 mol) of benzaldehyde (99%) were added thereto within 30 minutes. The reaction mixture was stirred at 60° C. for 4 hours. After cooling to 25° C., the lower aqueous phase was removed. From the organic phase remaining in the reactor, approx. 99 g of toluene/water were distilled off (azeotropic drying) at 25 to 45° C. and a pressure of 100 mbar. After the distillation, 99 g of fresh toluene were added again. There remained approx. 2282 g of a clear solution of benzaldehyde methylhydrazone in toluene.

635.6 g (2.70 mol) of ethyl 2-ethoxymethylene-4,4-difluoro-3-oxobutyrate (94.2% by weight) were added to this solution at 25 to 30° C. within 2 hours, and the mixture was stirred at 30° C. for another 1 hour. The resulting solution comprised 27.8% by weight of the desired ethyl 4,4-difluoro-2-[1-{N-methyl-N'[1-phenylmethylidene]hydrazino}-methylidene]-3-oxobutyrate (HPLC analysis).

17.6 g (0.054 mol) of sulfuric acid (30% in water) were added at 40° C. to this solution then the mixture was heated to 60° C. within 30 minutes and stirred at 60° C. for 2 hours. The resulting solution comprised 16.4% by weight of the desired ethyl 3-difluoro-methyl-1-methyl-1H-pyrazole-4-carboxylate (HPLC analysis, quantification with external standard).

1620 g (4.05 mol) of 10% by weight sodium hydroxide solution were metered into the solution at 60° C. and the mixture was stirred at 60° C. for 3 hours. After cooling to 25° C., the phases were separated. The toluenic upper phase comprised mainly the benzaldehyde released. The lower aqueous phase comprised, as the main component, the sodium salt of the desired 3-difluoromethyl-1-methyl-1H-pyrazole-4-carboxylic acid. The toluene phase was washed with 540 g of water. A further 1125 g of water were added to the combined water phases. Then 1277.5 g (3.91 mol) of sulfuric acid (30% in water) were then added to the aqueous carboxylate solution at 53 to 56° C. within 30 minutes, which precipitated the desired pyrazolecarboxylic acid. After cooling to 3° C., the solids were filtered off and washed with a total of 1880 g of water (25° C.) in portions. After drying (60° C., 20 mbar), 402.2 g of 3-difluoromethyl-1-methyl-1H-pyrazole-4-carboxylic acid were obtained in a purity of 99.4% by weight. The yield based on the molar amount of ethyl 2-ethoxymethylene-4,4-difluoro-3-oxobutyrate used was 84.2%. The undesired carboxylic acid isomer was no longer detectable.

EXAMPLE 8

Preparation of 3-difluoromethyl-1-methyl-1H-pyrazole-4-carboxylic Acid from P-Chlorobenzaldehyde, Methylhydrazine and Ethyl Ethoxymethylene-4,4-difluoro-3-oxobutyrate without Isolation/Purification of the Intermediates (One-Pot Method)

9.4 g (0.2 mol) of methylhydrazine (98%) were initially charged in 150.2 g of toluene. At room temperature, 28.11 g (0.2 mol) of p-chlorobenzaldehyde were added within 10 minutes, such that the temperature rose to 45 to 50° C. Subsequently, the mixture was stirred at 60° C. for a further 1 hour. The water phase was removed. From the toluene phase comprising the hydrazone, a sufficient amount of solvent was distilled off at 40° C. under reduced pressure for the solution to become clear (removal of residual water).

The remaining solution was made up with toluene to the original total mass and cooled to 3° C. At 3 to 6° C., 47.4 g (0.2 mol) of ethyl 2-ethoxymethylene-4,4-difluoro-3-oxobutyrate (93.8%) were added thereto within 45 min. The mixture was heated to 25° C. and stirred at this temperature for a further 15 hours. This formed a pale yellow suspension (precipitated ethyl 4,4-difluoro-2-[1-{N-methyl-N'[1-(4-chlorophenyl)-methylidene]hydrazine}methylidene]-3-oxobutyrate.

1.8 g of p-toluenesulfonic acid monohydrate (0.009 mol) were added to the suspension, and the mixture was stirred at 70° C. for 1 hour, which forms a clear solution. 250 g of 10% potassium hydroxide solution (0.45 mol) were added to this solution, and the mixture was stirred at 60° C. for 3 hours. After cooling to 25° C., the phases were separated. The toluene phase was washed twice with 50 g of water each time. The combined water phases were acidified at 50° C. with 60 g (0.52 mol) of concentrated hydrochloric acid (32% by weight) (pH<2), which precipitated the desired carboxylic acid. The solids were filtered off at 10° C. and washed with cold water. After the drying (60° C., 20 mbar), 26.3 g of 3-difluoromethyl-1-methyl-1H-pyrazole-4-carboxylic acid were obtained in a purity of 93.3% by weight. The yield based on the molar amount of methylhydrazine or ethyl 2-ethoxymethylene-4,4-difluoro-3-oxobutyrate used was 75.5%.

Analogously to example 8, the synthesis of 3-difluoromethyl-1-methyl-1H-pyrazole-4-carboxylic acid was performed by means of correspondingly substituted benzaldehydes and ketones:

| Example | Benzaldehyde/ketone | Yield [%[ | Purity [% by wt.] |
|---|---|---|---|
| 9 | o-chlorobenzaldehyde | 67.2 | 98.5 |
| 10 | p-methoxybenzaldehyde | 52.1 | 96.5 |
| 11 | p-methylbenzaldehyde | 70.7 | 100 |
| 12 | o-nitrobenzaldehyde[1] | 52.1 | n.d. |
| 13 | p-nitrobenzaldehyde[1] | 58.1 | n.d. |
| 14 | cyclohexanone | 71.5 | 100 |

[1]The reaction of the nitrobenzaldehyde with methylhydrazine to give the corresponding hydrazone was not conducted to complete conversion. The end product is therefore contaminated by nitrobenzaldehyde, which precipitated out of aqueous solutions as a solid together with 3-difluoromethyl-1-methyl-1H-pyrazole-4-carboxylic acid.

In analogy to the preparation of ethyl 4,4-difluoro-2-[1-{N-methyl-N'[1-phenylmethylidene]hydrazino}methylidene]-3-oxobutyrate (example 1, step 1.1), the following compounds of the formula VI were prepared:

EXAMPLE 15

Ethyl 4,4-difluoro-2-[1-{N-methyl-N'[1-(4-chlorophenyl)methylidene]-hydrazino}Methylidene]-3-oxobutyrate $^{13}$C NMR: 190.2, 181.5, 166.6, 164.6, 148.8, 144.8, 144.2, 135.2, 132.8, 128.9, 128.6, 110.4, 108.4, 107.2, 99.60, 60.51, 59.71, 40.08, 13.86.

EXAMPLE 16

Ethyl 4,4-difluoro-2-[1-{N-methyl-N'-[1-(2-chlorophenyl)methylidene]-hydrazino}Methylidene]-3-oxobutyrate $^{13}$C NMR: 190.3, 181.6, 166.4, 164.5, 148.6, 140.9, 140.2, 133.5, 132.1, 131.0, 130.0, 127.5, 127.4, 110.2, 108.3, 107.7, 100.3, 60.46, 59.77, 39.94, 13.74.

EXAMPLE 17

Ethyl 4,4-difluoro-2-[1-{N-methyl-N'-[1-(4-methoxyphenyl)methylidene]-hydrazino}methylidene]-3-oxobutyrate $^{13}$C NMR: 190.8, 181.1, 166.8, 164.8, 161.3, 148.7, 146.1, 145.5, 129.5, 126.4, 114.3, 110.4, 108.5, 106.4, 98.46, 60.36, 59.54, 55.30, 39.36, 13.86.

EXAMPLE 18

Ethyl 4,4-difluoro-2-[1-{N-methyl-N'-[1-(4-methylphenyl)methylidene]-hydrazino}methylidene]-3-oxobutyrate $^{13}$C NMR: 189.9, 181.2, 166.6, 164.6, 148.8, 146.1, 145.5, 140.7, 131.1, 129.4, 109.3, 108.4, 106.7, 98.82, 60.34, 59.54, 39.43, 21.00, 13.81.

EXAMPLE 19

Ethyl 4,4-difluoro-2-[1-{N-methyl-N'-[1-(2-nitrophenyl)methylidene]-hydrazino}methylidene]-3-oxobutyrate $^{13}$C NMR: 190.8, 181.8, 164.5, 164.4, 148.6, 148.3, 141.5, 140.6, 133.7, 132.8, 131.2, 128.6, 124.9, 110.2, 108.3, 108.1, 100.8, 60.51, 59.66, 39.33, 13.69.

EXAMPLE 20

Ethyl 4,4-difluoro-2-[1-{N-methyl-N'-[1-(4-nitrophenyl)methylidene]-hydrazino}methylidene]-3-oxobutyrate $^{13}$C NMR: 190.3, 181.8, 164.4, 148.1, 143.5, 142.9, 140.0, 139.8, 128.4, 124.0, 110.3, 108.2, 108.1, 100.8, 60.67, 59.89, 39.65, 14.15.

The compounds of examples 15 to 20 were, in analogy to example 1, step 1.2, converted to ethyl 3-difluoromethyl-1-methyl-1H-pyrazole-4-carboxylate, which was subsequently hydrolyzed to 3-difluoromethyl-1-methyl-1H-pyrazole-4-carboxylic acid.

The invention claimed is:
1. A process for preparing 1,3,4-substituted pyrazole compounds of the formula I

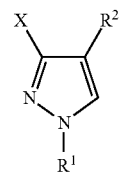

in which
X is a $CX^1X^2X^3$ group in which
  $X^1$, $X^2$ and $X^3$ are each independently hydrogen, fluorine or chlorine, where $X^1$ may also be $C_1$-$C_6$-alkyl or $C_1$-$C_4$-haloalkyl and where at least one of the $X^1$, $X^2$ radicals is different from hydrogen,
$R^1$ is $C_1$-$C_4$-alkyl or cyclopropyl, and
$R^2$ is CN or a $CO_2R^{2a}$ group in which
  $R^{2a}$ is $C_5$-$C_6$-cycloalkyl, optionally substituted phenyl or $C_1$-$C_6$-alkyl which may optionally be substituted by $C_1$-$C_4$-alkoxy, phenyl or $C_3$-$C_6$-cycloalkyl,
comprising
i) reacting a compound of the formula II with a hydrazone of the formula III

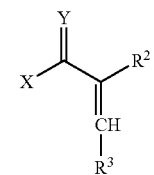

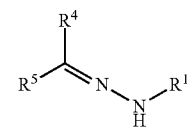

wherein
Y is oxygen, an $NR^{y1}$ group or an $[NR^{y2}R^{y3}]^+Z^-$ group, in which
  $R^{y1}$, $R^{y2}$ and $R^{y3}$ are each independently $C_1$-$C_6$-alkyl, $C_5$-$C_6$-cycloalkyl, optionally substituted phenyl or optionally substituted phenyl-$C_1$-$C_4$-alkyl, or
  $R^{y2}$ and $R^{y3}$ together with the nitrogen atom to which they are bonded are an N-bonded, 5- to 8-membered, saturated, optionally substituted heterocycle which, as well as the nitrogen atom, may also comprise 1 or 2 further heteroatoms selected from N, O and S as ring atoms, and
  $Z^-$ is an anion;
$R^3$ is $OR^{3a}$ or an $NR^{3b}R^{3c}$ group, in which
  $R^{3a}$, $R^{3b}$ and $R^{3c}$ are each independently $C_1$-$C_6$-alkyl, $C_5$-$C_6$-cycloalkyl, optionally substituted phenyl or optionally substituted phenyl-$C_1$-$C_4$-alkyl, or
  $R^{3b}$ and $R^{3c}$ together with the nitrogen atom to which they are bonded are an N-bonded 5- to 8-membered, saturated, optionally substituted heterocycle which, as well as the nitrogen atom, may also comprise 1 or 2 further heteroatoms selected from N, O and S as ring atoms, and $R^4$ and $R^5$ are each independently hydrogen, $C_1$-$C_6$-alkyl which may optionally be substituted by $C_1$-$C_4$-alkoxy, phenyl or $C_3$-$C_6$-cycloalkyl, $C_3$-$C_6$-cycloalkyl or optionally substituted phenyl, where at least one of the $R^4$ and $R^5$ radicals is different from hydrogen, or $R^4$ and $R^5$ together with the carbon atom to which they are bonded may also be a 5- to 10-membered saturated carbocycle which is optionally mono- or polysubstituted by $C_1$-$C_4$-alkyl groups and/or optionally substituted phenyl, and/or comprises one or 2 fused phenyl rings;

ii) treating the reaction product obtained with an acid in the presence of water.

2. The process according to claim 1, wherein compound III is prepared by reacting a carbonyl compound of the formula IV with a substituted hydrazine compound of the formula V

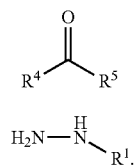

3. The process according to claim 1, wherein $R^3$ in formula II is O—$R^{3a}$ in which $R^{3a}$ is $C_1$-$C_4$-alkyl.

4. The process according claim 1, in which Y in formula II is oxygen.

5. The process according to claim 1, wherein X in the formulae I and II is a $CX^1X^2X^3$ group in which $X^1$ and $X^2$ are each fluorine and $X^3$ is hydrogen, fluorine or chlorine.

6. The process according to claim 1, wherein $R^2$ in the formulae I and II is a $COOR^{2a}$ group in which $R^{2a}$ is as defined above.

7. The process according to claim 1, in which $R^1$ is $C_1$-$C_4$-alkyl.

8. The process according to claim 1, in which
$R^4$ is hydrogen or $C_1$-$C_6$-alkyl and
$R^5$ is $C_1$-$C_6$-alkyl, $C_3$-$C_6$-cycloalkyl or optionally substituted phenyl, or
$R^4$ and $R^5$ together with the carbon atom to which they are bonded may be a 5- to 10-membered saturated carbocycle which is optionally mono- or polysubstituted by $C_1$-$C_4$-alkyl groups and/or comprises a fused phenyl ring.

9. The process according to claim 1, in which
$R^4$ R is hydrogen and
$R^5$ is optionally substituted phenyl.

10. A compound of the general formula VI

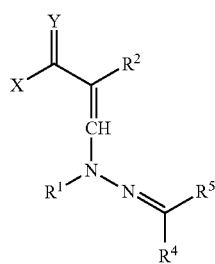

in which,

X is a $CX^1X^2X^3$ group in which
$X^1$, $X^2$ and $X^3$ are each independently hydrogen, fluorine or chlorine, where $X^1$ may also be $C_1$-$C_6$-alkyl or $C_1$-$C_4$-haloalkyl and where at least one of the $X^1$, $X^2$ radicals is different from hydrogen, Y is oxygen, an $NR^{y1}$ group or an $[NR^{y2}R^{y3}]^+Z^-$ group, in which
$R^{y1}$, $R^{y2}$ and $R^{y3}$ are each independently $C_1$-$C_6$-alkyl, $C_5$-$C_6$-cycloalkyl, optionally substituted phenyl or optionally substituted phenyl-$C_1$-$C_4$-alkyl, or
$R^{y2}$ and $R^{y3}$ together with the nitrogen atom to which they are bonded are an N-bonded, 5- to 8-membered, saturated, optionally substituted heterocycle which, as well as the nitrogen atom, may also comprise 1 or 2 further heteroatoms selected from N, O and S as ring atoms, and $Z^-$ is an anion;

$R^1$ is $C_1$-$C_4$-alkyl or cyclopropyl, and
$R^2$ is CN or a $CO_2R^{2a}$ group in which
$R^{2a}$ is $C_5$-$C_6$-cycloalkyl, optionally substituted phenyl or $C_1$-$C_6$-alkyl which may optionally be substituted by $C_1$-$C_4$-alkoxy, phenyl or $C_3$-$C_6$-cycloalkyl, and $R^4$ and $R^5$ are each independently hydrogen, $C_1$-$C_6$-alkyl which may optionally be substituted by $C_1$-$C_4$-alkoxy, phenyl or $C_3$-$C_6$-cycloalkyl, $C_3$-$C_6$-cycloalkyl or optionally substituted phenyl, where at least one of the $R^4$ and $R^5$ radicals is different from hydrogen, or $R^4$ and $R^5$ together with the carbon atom to which they are bonded may also be a 5- to 10-membered saturated carbocycle which is optionally mono- or polysubstituted by $C_1$-$C_4$-alkyl groups and/or optionally substituted phenyl, and/or comprises one or 2 fused phenyl rings;

excluding compounds of the formula VI in which $R^4$ and $R^5$ are each optionally substituted phenyl and Y is oxygen.

11. The compound according to claim 10, in which Y is oxygen.

12. The compound according to claim 10, in which X is a $CX^1X^2X^3$ group in which $X^1$ and $X^2$ are each fluorine and $X^3$ is hydrogen, fluorine or chlorine.

13. The compound according to claim 10, in which $R^2$ is a $COOR^{2a}$ group.

14. The compound according to claim 10, in which $R^1$ is $C_1$-$C_4$-alkyl.

15. The compound according to claim 10, in which
$R^4$ is hydrogen or $C_1$-$C_6$-alkyl and
$R^5$ is $C_1$-$C_6$-alkyl, $C_3$-$C_6$-cycloalkyl or optionally substituted phenyl, or
$R^4$ and $R^5$ together with the carbon atom to which they are bonded may be a 5- to 10-membered saturated carbocycle which is optionally mono- or polysubstituted by $C_1$-$C_4$-alkyl groups and/or comprises a fused phenyl ring.

16. The compound according to claim 10, in which
$R^4$ is hydrogen and
$R^5$ is optionally substituted phenyl.

17. The compound according to claim 10, in which
$R^4$ and $R^5$ together with the carbon atom to which they are bonded are a 5- to 10-membered saturated carbocycle which is optionally mono- or polysubstituted by $C_1$-$C_4$-alkyl groups.

18. A process for preparing a pyrazolecarboxylic acid of the formula Ia

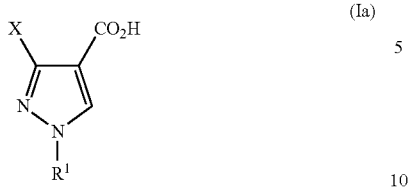

in which
X is a $CX^1X^2X^3$ group in which
  $X^1$, $X^2$ and $X^3$ are each independently hydrogen, fluorine or chlorine, where $X^1$ may also be $C_1$-$C_6$-alkyl or $C_1$-$C_4$-haloalkyl and where at least one of the $X^1$, $X^2$ radicals is different from hydrogen,
$R^1$ is $C_1$-$C_4$-alkyl or cyclopropyl, comprising
a) providing a compound of formula (I)

a)

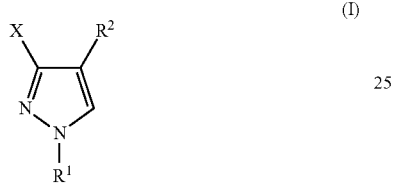

in which
X is a $CX^1X^2X^3$ group in which
  $X^1$, $X^2$ and $X^3$ are each independently hydrogen, fluorine or chlorine, where $X^1$ may also be $C_1$-$C_6$-alkyl or $C_1$-$C_4$-haloalkyl and where at least one of the $X^1$, $X^2$ radicals is different from hydrogen,
$R^1$ is $C_1$-$C_4$-alkyl or cyclopropyl,
$R^2$ is CN or a $CO_2R^{2a}$ group in which
  $R^{2a}$ is $C_5$-$C_6$-cycloalkyl, optionally substituted phenyl or $C_1$-$C_6$-alkyl which may optionally be substituted by $C_1$-$C_4$-alkoxy, phenyl or $C_3$-$C_6$-cycloalkyl; and
b) converting the compound I to a 1,3-substituted pyrazolecarboxylic acid of the formula Ia;
wherein said providing of compound of formula (I) comprises
  i) reacting a compound of the formula II with a hydrazone of the formula III

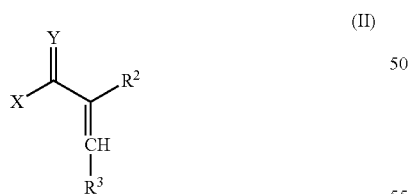

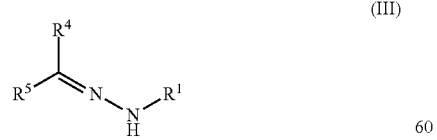

wherein
Y is oxygen, an $NR^{y1}$ group or an $[NR^{y2}R^{y3}]^+Z^-$ group, in which
  $R^{y1}$, $R^{y2}$ and $R^{y3}$ are each independently $C_1$-$C_6$-alkyl, $C_5$-$C_6$-cycloalkyl, optionally substituted phenyl or optionally substituted phenyl-$C_1$-$C_4$-alkyl, or $R^{y2}$ and $R^{y3}$ together with the nitrogen atom to which they are bonded are an N-bonded, 5- to 8-membered, saturated, optionally substituted heterocycle which, as well as the nitrogen atom, may also comprise 1 or 2 further heteroatoms selected from N, O and S as ring atoms, and
  $Z^-$ is an anion;
$R^3$ is $OR^{3a}$ or an $NR^{3b}R^{3c}$ group, in which
  $R^{3a}$, $R^{3b}$ and $R^{3c}$ are each independently $C_1$-$C_6$-alkyl, $C_5$-$C_6$-cycloalkyl, optionally substituted phenyl or optionally substituted phenyl-$C_1$-$C_4$-alkyl, or
  $R^{3b}$ and $R^{3c}$ together with the nitrogen atom to which they are bonded are an N-bonded 5- to 8-membered, saturated, optionally substituted heterocycle which, as well as the nitrogen atom, may also comprise 1 or 2 further heteroatoms selected from N, O and S as ring atoms, and
$R^4$ and $R^5$ are each independently hydrogen, $C_1$-$C_6$-alkyl which may optionally be substituted by $C_1$-$C_4$-alkoxy, phenyl or $C_3$-$C_6$-cycloalkyl, $C_3$-$C_6$-cycloalkyl or optionally substituted phenyl, where at least one of the $R^4$ and $R^5$ radicals is different from hydrogen, or
$R^4$ and $R^5$ together with the carbon atom to which they are bonded may also be a 5- to 10-membered saturated carbocycle which is optionally mono- or polysubstituted by $C_1$-$C_4$-alkyl groups and/or optionally substituted phenyl, and/or comprises one or 2 fused phenyl rings; and
  ii) treating the reaction product obtained with an acid in the presence of water.

19. A process for preparing a compound of the formula VII

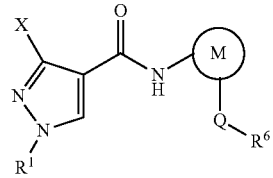

in which
X is a $CX^1X^2X^3$ group in which
  $X^1$, $X^2$ and $X^3$ are each independently hydrogen, fluorine or chlorine, where $X^1$ may also be $C_1$-$C_6$-alkyl or $C_1$-$C_4$-haloalkyl and where at least one of the $X^1$, $X^2$ radicals is different from hydrogen,
$R^1$ is $C_1$-$C_4$-alkyl or cyclopropyl,
M is thienyl or phenyl which may bear a halogen substituent;
Q is a direct bond, cyclopropylene, a fused bicyclo[2.2.1]heptane or bicyclo[2.2.1]heptene ring;
$R^6$ is hydrogen, halogen, $C_1$-$C_4$-alkyl, $C_1$-$C_4$-haloalkoxy, mono- to trisubstituted phenyl, where the substituents are each independently selected from halogen and trifluoromethylthio, or cyclopropyl;
comprising
a) providing a compound of the formula (I), b)

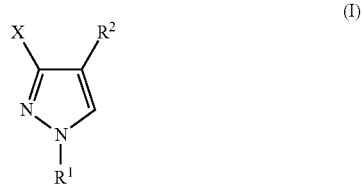

in which

X is a $CX^1X^2X^3$ group in which $X^1$, $X^2$ and $X^3$ are each independently hydrogen, fluorine or chlorine, where $X^1$ may also be $C_1$-$C_6$-alkyl or $C_1$-$C_4$-haloalkyl and where at least one of the $X^1$, $X^2$ radicals is different from hydrogen, $R^1$ is $C_1$-$C_4$-alkyl or cyclopropyl, $R^2$ is CN or a $CO_2R^{2a}$ group in which $R^{2a}$ is $C_5$-$C_6$-cycloalkyl, optionally substituted phenyl or $C_1$-$C_6$-alkyl which may optionally be substituted by $C_1$-$C_4$-alkoxy, phenyl or $C_3$-$C_6$-cycloalkyl;

b) converting the compound of formula (I) to a 1,3-substituted pyrazolecarboxylic acid of the formula Ia,

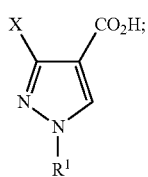

(Ia)

c) optionally converting the compound Ia to its acid halide, and d) reacting the compound of the formula Ia or its acid halide with an amine compound of the formula VIII,

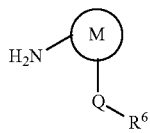

(VIII)

wherein said providing of compound of formula (I) comprises reacting a compound of the formula II with a hydrazone of the formula III

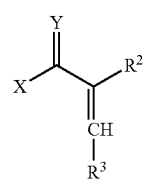

(II)

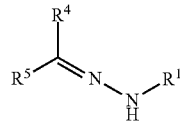

(III)

wherein

Y is oxygen, an $NR^{y1}$ group or an $[NR^{y2}R^{y3}]^{+Z-}$ group, in which $R^{y1}$, $R^{y2}$ and $R^{y3}$ are each independently $C_1$-$C_6$-alkyl, $C_5$-$C_6$-cycloalkyl, optionally substituted phenyl or optionally substituted phenyl-$C_1$-$C_4$-alkyl, or $R^{y2}$ and $R^{y3}$ together with the nitrogen atom to which they are bonded are an N-bonded, 5- to 8-membered, saturated, optionally substituted heterocycle which, as well as the nitrogen atom, may also comprise 1 or 2 further heteroatoms selected from N, O and S as ring atoms, and $Z^-$ is an anion;

$R^3$ is $OR^{3a}$ or an $NR^{3b}R^{3c}$ group, in which $R^{3a}$, $R^{3b}$ and $R^{3c}$ are each independently $C_1$-$C_6$-alkyl, $C_5$-$C_6$-cycloalkyl, optionally substituted phenyl or optionally substituted phenyl-$C_1$-$C_4$-alkyl, or $R^{3b}$ and $R^{3c}$ together with the nitrogen atom to which they are bonded are an N-bonded 5- to 8-membered, saturated, optionally substituted heterocycle which, as well as the nitrogen atom, may also comprise 1 or 2 further heteroatoms selected from N, O and S as ring atoms, and $R^4$ and $R^5$ are each independently hydrogen, $C_1$-$C_6$-alkyl which may optionally be substituted by $C_1$-$C_4$-alkoxy, phenyl or $C_3$-$C_6$-cycloalkyl, $C_3$-$C_6$-cycloalkyl or optionally substituted phenyl, where at least one of the $R^4$ and $R^5$ radicals is different from hydrogen, or $R^4$ and $R^5$ together with the carbon atom to which they are bonded may also be a 5- to 10-membered saturated carbocycle which is optionally mono- or polysubstituted by $C_1$-$G_4$-alkyl groups and/or optionally substituted phenyl, and/or comprises one or 2 fused phenyl rings; and iv) treating the reaction product obtained with an acid in the presence of water.

20. The process according to claim 6, wherein $R^2$ in the formulae I and II is a $COOR^{2a}$ group in which $R^{2a}$ is $C_1$-$C_6$-alkyl or $C_1$-$C_4$-alkoxy-$C_1$-$C_6$-alkyl.

21. The process according to claim 20, in which $R^1$ is methyl.

22. The compound according to claim 13, in which $R^2$ is a $COOR^{2a}$ group in which $R^{2a}$ is $C_1$-$C_6$-alkyl or $C_1$-$C_4$-alkoxy-$C_1$-$C_6$-alkyl.

23. The compound according to claim 22, in which $R^1$ is methyl.

\* \* \* \* \*

UNITED STATES PATENT AND TRADEMARK OFFICE
CERTIFICATE OF CORRECTION

PATENT NO. : 8,598,222 B2  Page 1 of 1
APPLICATION NO. : 12/990340
DATED : December 3, 2013
INVENTOR(S) : Wolf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 370 days.

Signed and Sealed this

Twenty-second Day of September, 2015

Michelle K. Lee
*Director of the United States Patent and Trademark Office*